US009522034B2

(12) United States Patent
Johnson et al.

(10) Patent No.: US 9,522,034 B2
(45) Date of Patent: Dec. 20, 2016

(54) LARGE VOLUME TISSUE REDUCTION AND REMOVAL SYSTEM AND METHOD

(71) Applicant: Eximis Surgical, LLC, Louisville, CO (US)

(72) Inventors: Kristin D. Johnson, Louisville, CO (US); William N. Gregg, Superior, CO (US); Dirk Johnson, Louisville, CO (US)

(73) Assignee: EXIMIS SURGICAL, LLC, Louisville, CO (US)

( * ) Notice: Subject to any disclaimer, the term of this patent is extended or adjusted under 35 U.S.C. 154(b) by 0 days.

(21) Appl. No.: 14/805,358

(22) Filed: Jul. 21, 2015

(65) Prior Publication Data
US 2016/0022352 A1 Jan. 28, 2016

Related U.S. Application Data

(60) Provisional application No. 62/027,645, filed on Jul. 22, 2014, provisional application No. 62/104,969, filed on Jan. 19, 2015.

(51) Int. Cl.
*A61B 18/14* (2006.01)
*A61B 17/22* (2006.01)
(Continued)

(52) U.S. Cl.
CPC ...... *A61B 18/14* (2013.01); *A61B 2017/00287* (2013.01); *A61B 2017/00867* (2013.01);
(Continued)

(58) Field of Classification Search
CPC ............... A61B 2018/141; A61B 2018/1422; A61B 2018/144; A61B 2018/00107; A61B 2018/00148
See application file for complete search history.

(56) References Cited

U.S. PATENT DOCUMENTS 4,368,734 A 1/1983 Banko
5,312,416 A 5/1994 Spaeth et al.
(Continued)

FOREIGN PATENT DOCUMENTS

EP 1004277 A1 5/2000
WO 2005122938 A1 12/2005
(Continued)

OTHER PUBLICATIONS

Megger. A Stitch in Time: The Complete Guide to Electrical Insulation Testing, C 2006, Megger, https://www.instrumart.com/assets/Megger-insulationtester.pdf, last accessed Jun. 8, 2016.*
(Continued)

*Primary Examiner* — Ronald Hupczey, Jr.
*Assistant Examiner* — Bo Ouyang
(74) *Attorney, Agent, or Firm* — Neugeboren O'Dowd PC

(57) ABSTRACT

A tissue removal system for extracting a tissue specimen from a patient is disclosed. The system has a retrieval bag, a first electrode, and a return electrode. The retrieval bag has a flexible container with an opening. The first electrode is coupled to an interior of the flexible container, and has a conductive wire with an exposure area, a first load-bearing area, a coating having a first active electrode surface area, and an impedance that is greater than an impedance of the conductive wire. The first active electrode surface area is less than the exposure area. The coating is configured to degrade during application of electrosurgical power and wherein the degradation expands the first active electrode surface area during the application of the electrosurgical power.

30 Claims, 23 Drawing Sheets

(51) Int. Cl.
  *A61B 17/24* (2006.01)
  *A61B 17/00* (2006.01)
  *A61B 18/00* (2006.01)
  *A61B 18/12* (2006.01)
(52) U.S. Cl.
  CPC ........... *A61B 2018/00083* (2013.01); *A61B 2018/00107* (2013.01); *A61B 2018/00172* (2013.01); *A61B 2018/00601* (2013.01); *A61B 2018/1213* (2013.01)

(56) References Cited

U.S. PATENT DOCUMENTS

| | | | |
|---|---|---|---|
| 5,354,303 | A | 10/1994 | Spaeth et al. |
| 5,569,284 | A | 10/1996 | Young et al. |
| 5,611,803 | A * | 3/1997 | Heaven ............ A61B 17/00234 606/110 |
| 5,643,283 | A | 7/1997 | Younker |
| 5,735,289 | A | 4/1998 | Pfeffer et al. |
| 5,814,044 | A | 9/1998 | Hooven |
| 5,836,953 | A | 11/1998 | Yoon |
| 5,868,740 | A | 2/1999 | LeVeen et al. |
| 5,968,040 | A | 10/1999 | Swanson et al. |
| 6,280,450 | B1 | 8/2001 | McGuckin |
| 6,383,196 | B1 | 5/2002 | Leslie et al. |
| 6,537,273 | B1 | 3/2003 | Sosiak et al. |
| 6,685,628 | B2 | 2/2004 | Vu |
| 6,752,811 | B2 | 6/2004 | Chu et al. |
| 7,004,942 | B2 | 2/2006 | Laird et al. |
| 7,052,501 | B2 | 5/2006 | McGuckin et al. |
| 7,474,909 | B2 | 1/2009 | Phan et al. |
| 7,753,920 | B2 | 7/2010 | McGuckin et al. |
| 8,192,436 | B2 | 6/2012 | Schmitz et al. |
| 8,386,006 | B2 | 2/2013 | Schouenborg |
| 8,758,349 | B2 | 6/2014 | Germain et al. |
| 2002/0068943 | A1 | 6/2002 | Chu et al. |
| 2002/0095152 | A1 | 7/2002 | Ciarrocca et al. |
| 2004/0002683 | A1 | 1/2004 | Nicholson et al. |
| 2004/0162554 | A1 | 8/2004 | Lee et al. |
| 2005/0267492 | A1 | 12/2005 | Poncet et al. |
| 2006/0167470 | A1 | 7/2006 | McGuckin |
| 2007/0088370 | A1 | 4/2007 | Kahle et al. |
| 2008/0027428 | A1 * | 1/2008 | Palanker ............ A61B 18/1402 606/45 |
| 2008/0221604 | A1 | 9/2008 | Kondoh et al. |
| 2009/0149851 | A1 * | 6/2009 | Craig ................ A61B 18/1402 606/42 |
| 2009/0149865 | A1 | 6/2009 | Schmitz et al. |
| 2009/0192510 | A1 * | 7/2009 | Bahney ............ A61B 17/32056 606/45 |
| 2009/0326546 | A1 * | 12/2009 | Mohamed ........ A61B 17/00234 606/114 |
| 2010/0145329 | A1 * | 6/2010 | Bystryak ............ A61B 18/1206 606/33 |
| 2011/0040314 | A1 | 2/2011 | McGuckin, Jr. et al. |
| 2011/0087235 | A1 | 4/2011 | Taylor et al. |
| 2011/0184311 | A1 | 7/2011 | Parihar et al. |
| 2011/0184432 | A1 | 7/2011 | Parihar et al. |
| 2011/0184433 | A1 | 7/2011 | Parihar et al. |
| 2011/0184435 | A1 | 7/2011 | Parihar et al. |
| 2012/0083796 | A1 | 4/2012 | Grover et al. |
| 2013/0041373 | A1 | 2/2013 | Laufer |
| 2013/0123783 | A1 * | 5/2013 | Marczyk ............ A61B 17/29 606/45 |
| 2013/0131445 | A1 | 5/2013 | Zerfas et al. |
| 2014/0052018 | A1 | 2/2014 | Hawkins |
| 2014/0249541 | A1 | 9/2014 | Kahle et al. |
| 2014/0276801 | A1 * | 9/2014 | Juergens ............ A61N 1/04 606/42 |
| 2014/0276913 | A1 | 9/2014 | Tah et al. |
| 2014/0288486 | A1 | 9/2014 | Hart et al. |
| 2016/0030073 | A1 | 2/2016 | Isakov et al. |

FOREIGN PATENT DOCUMENTS

| | | | |
|---|---|---|---|
| WO | 2014158880 | A1 | 10/2014 |
| WO | 2015084769 | A1 | 6/2015 |

OTHER PUBLICATIONS

Olympus America Medical, "Four-Wire Basket", Webpage found at http://medical.olympusannerica.com/products/basket/four-wire-basket Inventor(s) aware of prior art on or before Sep. 30, 2015, p. 2, Published in: US.

Applied Medical, "Alexis Contained Extraction System", Webpage found at http://appliedmedical.com/products/Alexis_CES.aspx Inventor(s) aware of prior art on or before Sep. 30, 2015, p. 1, Published in: US.

Barbieri, Robert L., "Options for reducing the use of open power morcellation of uterine tumors", Webpage found at http://www.obgmanagement.com/home/article/options-for-reducing-the-use-of-open-power-morcellation-of-uterine-tumors/acad25997062986d1ffdc157327381ef.html Inventor(s) aware of prior art on or before Sep. 30, 2015, 2014, p. 5, Publisher: OBG Management.

Covidien, "Principals of Electrosurgery", Webpage found at http://www.asit.org/assets/documents/Prinicpals_in_electrosurgery.pdf Inventor(s) aware of prior art on or before Sep. 30, 2015, 2008, p. 28, Publisher: Covidien AG, Published in: US.

Duck, A .Francis, "Physical Properties of Tissue", 2012, p. 5, Publisher: IPEM, Published in: US.

Covidien, "Endobag Specimen Retrieval System", Webpage found at http://www.covidien.com/surgical/products/hand-instruments-and-ligation/specimen-retrieval-products Inventor(s) aware of prior art on or before Sep. 30, 2015, p. 2, Published in: US.

Covidien, "Endo Catch 15mm Specimen Pouch", Webpage found at http://products.covidien.com/pages.aspx?page=ProductDetail&id=13463&cat=Devices&cat2=Model Inventor(s) aware of prior art on or before Sep. 30, 2015, p. 2, Published in: US.

Covidien, "Endo Catch Gold", Webpage found at http://www.covidien.com/surgical/products/hand-instruments-and-ligation/specimen-retrieval-products Inventor(s) aware of prior art on or before Sep. 30, 2015, p. 2, Published in: US.

Ethicon, "Endopouch Specimen Retrieval Bag", Webpage found at http://www.ethicon.com/healthcare-professionals/products/other/lap-hand/specimen-retrieval Inventor(s) aware of prior art on or before Sep. 30, 2015, p. 2, Published in: US.

Friedrichs, et al., "A New Dual Current-Mode Controller Improves Power Regulation in Electrosurgical Generators", "Transactions on Biomedical Circuits and Systems", Feb. 2012, p. 6, Publisher: IEEE, Published in: US.

Hackethal, Veronica, "Morcellation Isolation Bag: Expert Questions Technique", Webpage found at http://www.medscape.com/viewarticle/829476 Inventor(s) aware of prior art on or before Sep. 30, 2015, Aug. 6, 2014, p. 2, Publisher: Medscape.

Heim, Warren P., "How Electrosurgery Really Cuts Tissue", "www.TeamMedical.us", Jan. 8, 2015, p. 3, Publisher: Team Medical, LLC, Published in: US.

Applied Medical, "Inzii Retrieval Systems", Webpage found at http://www.appliedmedical.com/Products/Inzii.aspx Inventor(s) aware of prior art on or before Sep. 30, 2015, p. 1, Published in: US.

Isakov, et al., "A New Laparoscopic Morcellator Using an Actuated Wire Mesh and Bag", "Journal of Medical Devices", Mar. 2014, p. 7, Publisher: ASME, Published in: US.

Karl Storz, "Urology", Webpage found at https://www.karlstorz.com/us/en/urology.htm Inventor(s) aware of prior art on or before Sep. 30, 2015, p. 7, Published in: US.

Cook Medical, "LapSac Surgical Tissue Pouch", Webpage found at https://www.cookmedical.com/products/uro_lapsac_webds/ Inventor(s) aware of prior art on or before Sep. 30, 2015, p. 2, Published in: US.

Lattis Surgical, "Lattis Contained Tissue Extraction (CTE Device)", Webpage found at http://www.lattissurgical.com/lattis-cte-vs.-morcellation.html Inventor(s) aware of prior art on or before Sep. 30, 2015, 2015, p. 1.

(56) References Cited

OTHER PUBLICATIONS

Lina Medical, "LinA Bipolar Loop", Webpage found at http://www.lina-medical.com/products/lina-loop-range/lina-bipolar-loop/ Inventor(s) aware of prior art on or before Sep. 30, 2015, p. 6, Published in: US.

Lina Medical, "LiNA Gold Loop", Webpage found at http://www.lina-medical.com/products/lina-loop-range/lina-gold-loop/ Inventor(s) aware of prior art on or before Sep. 30, 2015, p. 6.

Lina Medical, "LiNA Gold Loop HC", Webpage found at http://www.lina-medical.com/products/lina-loop-range/lina-gold-loop-hc/ Inventor(s) aware of prior art on or before Sep. 30, 2015, p. 6, Published in: US.

Mechcatie, Elizabeth, "Study finds insufflated collection bag successfully used in power morcellation cases", Webpage found at http://www.obgynnews.com/home/article/study-finds-insufflated-collection-bag-successfully-used-in-power-morcellation-cases/301a306877e1c40b290e2e946fb8a603.html Inventor(s) aware of prior art on or before Sep. 30, 2015, Aug. 5, 2014, p. 2, Publisher: Ob.Gyn. News.

Tissue Extraction Task Force, "Morcellation During Uterine Tissue Extraction", "AAGL Advancing Minimally Invasive Gynecology Worldwide", May 6, 2014, p. 15, Publisher: AAGL.

Palanker, et al., "Electrosurgery With Cellular Precision", "Transactions on Biomedical Engineering", Feb. 2008, p. 4, Publisher: IEEE.

Pearce, John A., "Electrosurgery", "Biomedical Engineering Program", 1986, p. 20, Publisher: University of Texas at Austin, Published in: US.

Olympus America Medical, "PKS PlasmaSORD", Webpage found at http://medical.olympusamerica.com/products/handpiece/pks-plasmasord-962000pk Inventor(s) aware of prior art on or before Sep. 30, 2015, p. 2, Published in: US.

Olympus America Medical, "PKS Bill", Webpage found at http://medical.olympusamerica.com/products/pks-bill-bI0533 Inventor(s) aware of prior art on or before Sep. 30, 2015, p. 2.

Olympus America Medical, "PolyLoop", Webpage found at http://medical.olympusamerica.com/products/polyloop Inventor(s) aware of prior art on or before Sep. 30, 2015, p. 2, Published in: US.

Cook Medical, "Disposable Hysteroscopic Polyp Snare", Webpage found at https://www.cookmedical.com/products/wh_dhps_webds/ Inventor(s) aware of prior art on or before Sep. 30, 2015, p. 2, Published in: US.

Olympus America Medical, "Resection in Saline Electrodes", Webpage found at http://medical.olympusamerica.com/products/resection-saline-electrodes Inventor(s) aware of prior art on or before Sep. 30, 2015, p. 2, Published in: US.

Olympus America Medical, "SnareMaster", Webpage found at http://medical.olympusamerica.com/products/snaremaster Inventor(s) aware of prior art on or before Sep. 30, 2015, p. 2.

Olympus America Medical, "Stiff Wire Basket", Webpage found at http://medical.olympusamerica.com/products/basket/stiff-wire-basket-fg-402q Inventor(s) aware of prior art on or before Sep. 30, 2015, p. 1, Published in: US.

Young, Lee W., "WO International Search Report and Written Opinion re Application No. PCTUS1541407", Nov. 27, 2015, p. 14, Published in: WO.

Copenheaver, Blaine R., International Search Report and Written Opinion re Application No. PCT/2014/020649, Mar. 14, 2013, p. 15, Published in: US.

* cited by examiner

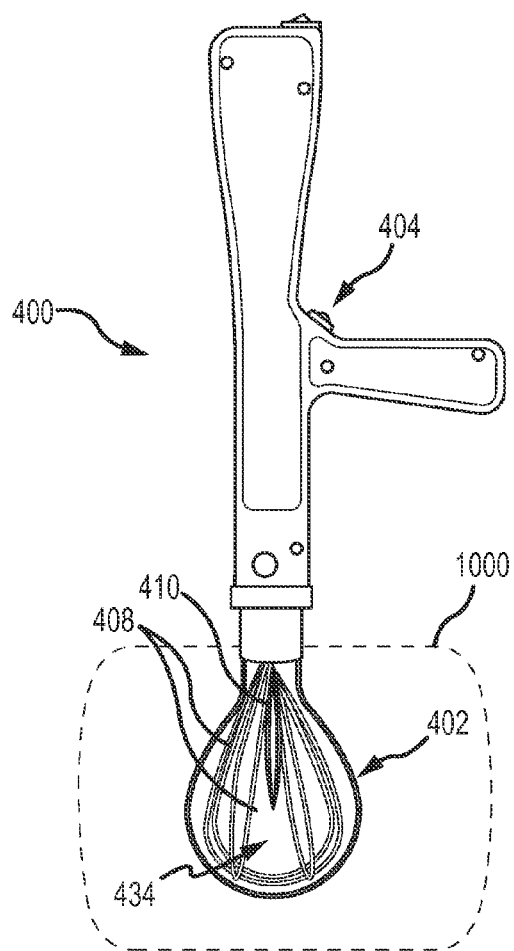
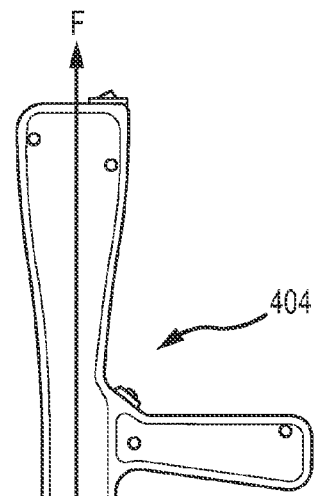
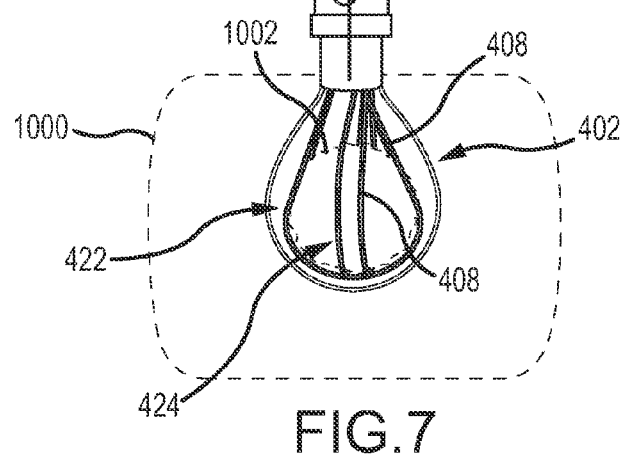
FIG.6
FIG.7

LARGE VOLUME TISSUE REDUCTION AND REMOVAL SYSTEM AND METHOD

CROSS-REFERENCE TO RELATED APPLICATIONS

This application claims priority to U.S. Provisional Application No. 62/027,645 filed Jul. 22, 2014 and entitled LARGE VOLUME TISSUE REDUCTION AND REMOVAL SYSTEM AND METHOD, and U.S. Provisional Application No. 62/104,969 filed Jan. 19, 2015 and entitled LARGE VOLUME TISSUE REDUCTION AND REMOVAL SYSTEM AND METHOD, the entire disclosures of which are hereby incorporated by reference for all proper purposes, as if fully set forth herein.

FIELD OF THE INVENTION

This invention is related to surgical devices. In particular, but not by way of limitation, the invention is related to large volume tissue removal.

BACKGROUND

Current methods for removing large tissue specimens with minimally invasive procedures such as, but not limited to, hysterectomy, nephrectomy, and splenectomy are to use morcellators or to manually reduce the tissue size with RF energy, mechanical cutting or fracture methods. These methods require a considerable amount of time and many sequential steps to complete. An alternative to the morcellator technique is to create a larger incision for the access port so that the tissue specimen can be removed in whole. Unfortunately this approach leads to more patient pain and longer recovery times.

SUMMARY

In some aspects, a tissue removal system for extracting a tissue specimen from a patient is disclosed. The system has a retrieval bag, a first electrode, and a return electrode. The retrieval bag has a flexible container with an opening. The first electrode is coupled to an interior of the flexible container, and has a conductive wire with an exposure area, a first load-bearing area, a coating having a first active electrode surface area, and an impedance that is greater than an impedance of the conductive wire. The first active electrode surface area is less than the exposure area. The coating is configured to degrade during application of electrosurgical power and wherein the degradation expands the first active electrode surface area during the application of the electrosurgical power.

In some aspects, the system has a tissue retrieval bag, a first electrode set, a second electrode set, an actuator, and a return electrode. The tissue retrieval bag has a flexible container with an opening. The first electrode set may have a plurality of electrodes removably coupled to an interior of the flexible container, each of the plurality of electrodes having a conductive wire with a load-bearing area. At least one of the plurality of electrodes may have a high impedance coating, an exposure area, and a first active electrode surface area, the first active electrode surface area less than the load-bearing area. The second electrode set may have a plurality of electrodes removably coupled to the interior of the flexible container. The actuator may have a first pull assembly coupled to a proximal portion of the first electrode set, and may be configured to apply a first pull force on the first electrode set. A second pull assembly may be coupled to a proximal portion of the second electrode set and configured to apply a second pull force on the second electrode set. The actuator may be configured to commence applying the first pull force prior to commencing applying the second pull force.

In some aspects, the system has a retrieval bag having a flexible container with an opening, a first electrode, and a return electrode. The first electrode may be coupled to an interior of the flexible container. The first electrode may have a conductive wire with a coating having a first active electrode surface area, an exposure area, and an impedance that is greater than an impedance of the conductive wire, wherein the first active electrode surface area is less than the exposure area. The exposure area may comprise a region of the coating that has a plurality of micro voids, has a reduced impedance, has a reduced thickness, exposes the conductive wire, or any combination thereof.

In some aspects, a method of extracting a tissue specimen from a patient is disclosed, wherein the specimen has a cross section that is larger than a cross section of a passage through which the specimen is to be extracted. The method may include introducing a tissue removal system, deploying the system, loading a specimen, exteriorizing a bag opening, applying a power, segmenting the specimen, and extracting the specimen. Introducing a tissue removal system into a cavity of the patient includes introducing a tissue removal system having a retrieval bag and a plurality of electrodes, at least one of the plurality of electrodes having a high impedance coating configured to allow an electrosurgical current to flow when a set of conditions are satisfied. Applying power includes applying an electrosurgical power that satisfies the set of conditions to the at least one of the plurality of electrodes to cause current to flow across an active electrode surface area of the at least one of the plurality of electrodes. Segmenting includes segmenting the specimen by applying the electrosurgical power to a surface area of the specimen in contact with the active electrode surface area of the at least one of the plurality of electrodes and applying a mechanical force to a surface area of the specimen in contact with the at least one of the plurality of electrodes. Extracting includes extracting the segmented specimen through the exteriorized opening of the retrieval bag.

BRIEF DESCRIPTION OF THE DRAWINGS

FIG. 6 illustrates another exemplary tissue removal device deployed about a specimen;

FIG. 7 illustrates the device of FIG. 6 in an exteriorized state;

DETAILED DESCRIPTION

Figure 1:
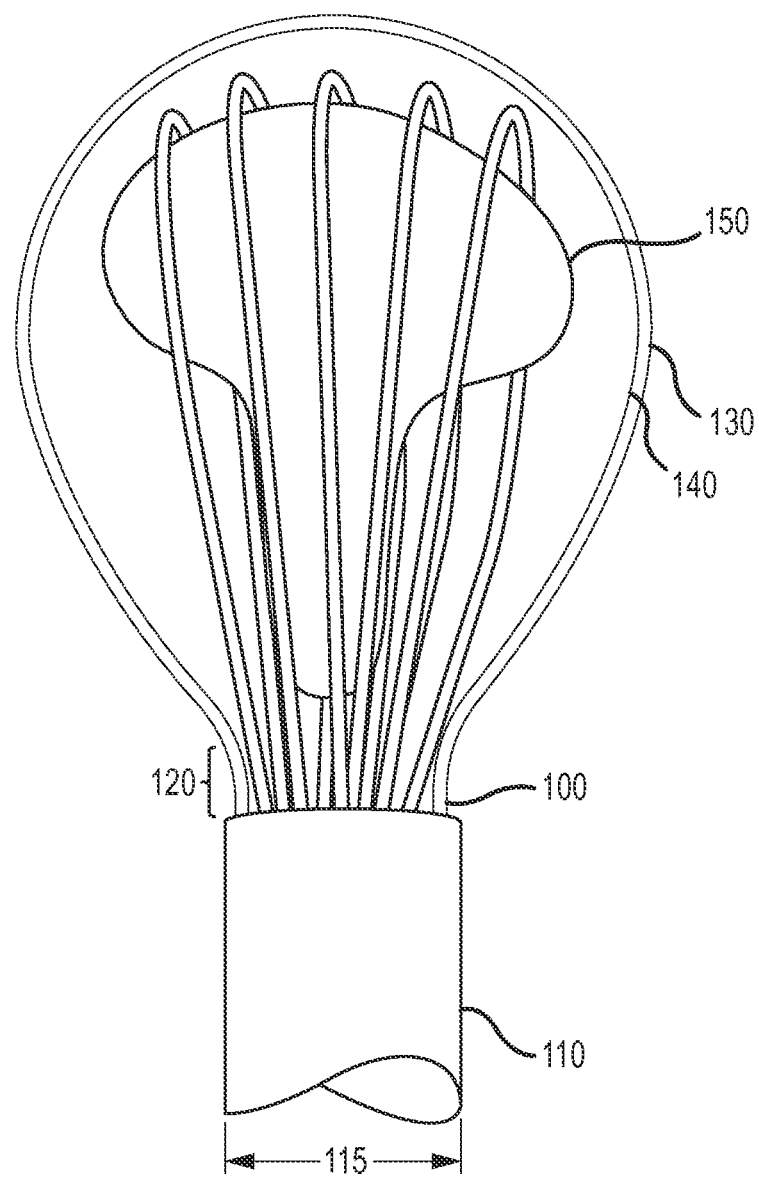
FIG. 1 illustrates a side view of an exemplary tissue removal device deployed about a specimen.

In order to decrease time and money associated with large tissue specimen removal, a new large volume tissue removal system and method were created. With the new system and method comes the additional benefit of containing the specimen in a bag, reducing the possibility of seeding cancerous cells into unaffected tissue due to the uncontrolled fragmentation occurring in morcellation or other tissue reduction practices. Furthermore, the probability of a minimally invasive surgical approach being performed, with smaller incisions in procedures where cancer is suspected, is increased. Since the system and method described herein comprise minimally-invasive procedures, recovery time from the use of such a system and method is decreased.

The new system also has the advantage of allowing for subsequent "reassembly" of the tissue segments by a pathologist. This is due to more controlled cutting of the tissue versus methods used today. It can be further aided through the use of a colorant or dye on the wires or bag that marks the tissue segments and their orientation to other segments.

One embodiment of the invention comprises a tissue specimen removal system. In such a system, a large volume tissue specimen is reduced in size and subsequently removed through an access port in the patient during minimally invasive surgery. One such system may be comprised of a device and one or more RF electrosurgical generators. The device may comprise a single-use device and may be used to introduce and deploy a specimen bag to capture and contain the tissue specimen during the procedure. The device may further be adapted to perform the cutting or tissue reduction through RF energy-charged wires, with the RF energy being received from the RF electrosurgical generator. One device may also comprise a handle portion which may comprise user controls, with the user controls being adapted to deploy and retract the wires and specimen bag and activate/deactivate the RF energy. The RF electrosurgical generator is used to deliver RF energy to the device to perform the cutting and reduce the tissue into smaller segments. After tissue reduction is completed, the device is removed, leaving the tissue segments contained in the bag. The bag is pulled through the access port and a tissue grasper is used to remove the pieces.

Another embodiment of the invention may comprise a method of using a tissue specimen removal system. One such method may introduce and deploy the device into the patient. The method may then comprise capturing and containing the tissue specimen with the specimen bag. After this method step the method may then allow the user to exteriorize the opening of the bag by using a string or guide wire as a means of directing the bag opening around the lumen. After this method step the method may comprise cutting and thereby reducing the specimen. At this point the method may comprise removal of the device then removal of the tissue segments. Another method for using a tissue specimen removal system includes introduction and deployment of the device into the patient. The method may then comprise capturing the tissue specimen within the specimen bag that has wires attached, bringing the opening of the bag outside of the patient, attaching a second instrument that applies the appropriate load and RF energy to the wires in the bag. At this point the cutting and reducing of the specimen occurs, the second device is removed and a grasper or other means is used to remove the tissue segments from the bag.

Turning now to FIG. 1, seen is at least a portion of one embodiment of the device 100 with the device comprising an outer lumen 110 that will be used to introduce the device 100 into the access port, either a trocar, small incision or natural opening within the patient, and a handle (not shown in FIG. 1) that will allow a surgeon to apply a force necessary to insert the device to the trocar/opening and to control a distal end 120 to the desired depth and location. The diameter 115 of the lumen 110 may be limited by diameter of the trocar/opening and the size of the contents within the device 100. The distal end 120 may comprise a shape adapted to avoid injury when inserted into the body. Furthermore, the distal end 120 may be adapted for manipulation within a body cavity during use.

In one embodiment, the outer lumen 110 may comprise a tissue specimen bag 130 and a plurality of wires 140, prior to deploying the bag 130 and wires 140 around a tissue specimen 150, as seen in FIG. 1. One tissue specimen 150 may comprise a uterus. The wires 140 may be used as active electrodes to deliver RF energy to the tissue specimen 150 and may comprise a return electrode. One or more return electrodes are located on the surface of the bag 130, integrated into the layers of the bag 130, as a separate electrode placed into or in contact with the tissue specimen 150 by the user through the lumen 110, within the bag 130 or on the device 100. When the device 100 has been introduced to the patient and the distal end 120 is in a proper location for deployment of the device 100, the bag 130 and wires 140 are deployed around the specimen 150. The bag 130, wires 140, and any associated deployment features may be referred to herein as a containment mechanism. In one embodiment, the bag 130 and wires 140 may be extended through the distal end 120 of the device 100 by activating a feature in the handle. This feature can be activated by applying a force at the handle mechanically transferred to the containment mechanism or can be advanced by rotationally advancing a threaded drive mechanism connected to the containment mechanism either manually or with by an electromechanical rotational drive component.

Figure 2:
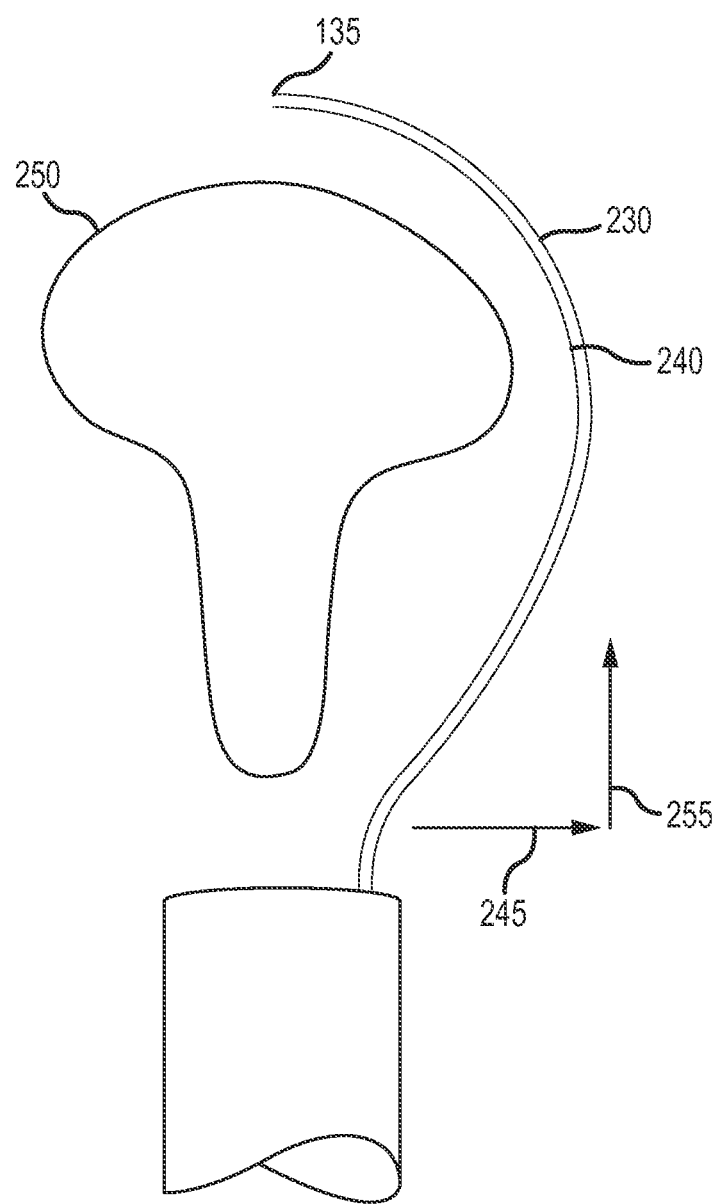
FIG. 2 illustrates a side view of another exemplary tissue removal device deployed near a specimen.

Seen in FIG. 2 is one initial deployment position. For example, the bag 230 and wires 240 may be extended towards a side of the specimen 250. Although the bag 230 and wires 240 are seen in FIG. 2 as being deployed to same side of the specimen 250, it is contemplated that the bag 230 and wires 240 may be deployed to different sides of the specimen 250. After deployment to the initial deployment position, the bag 230 may be opened to the final position seen in FIG. 1. For example, the bag 230 may be opened through the use of a spring force upon advancing the bag 130 from the distal end of the handle or through an introducer mechanism. The bag 230 may also be opened through enabling a spring force associated with the electrode wires (e.g., the wires may be a spring Nitinol wire). The bag 230 may be further opened by the surgeon with a mechanism separate from the device 100 such as, but not limited to, a grasper. A bag distal end 135 may be moved from the lumen 110 to the initial deployment position by activating a feature in the handle, such a feature may comprise a "scooping motion" adapted to extend bag 230 in a first direction 255 and a second direction 245, which may aid in the capture of the specimen 250. In another embodiment, the bag 130 has a side opening in which the bag can be opened by separating the sides of the opening along a dimension of the bag parallel to the wires after deployment. This allows the wires to be moved out of the way from the tissue as it is inserted into the bag by the user using a grasper or other device. After the tissue specimen is inserted, the side opening is closed.

In one embodiment, the wires 240 may be temporarily or semi-permanently coupled to an inner bag surface to aid in specimen 250 capture. This coupling may be created with an adhesive, a heat staking or welding process, formed or melted into the bag or bag surface, a design feature in the bag, such as a sleeve or a serration that can be formed or applied as an additional laminated layer. With this embodiment, the wires would be geometrically arranged around the inner surface of the bag so that the intended spacing for the cut is maintained while the tissue specimen is placed into the bag. An additional embodiment would be to arrange multiple wires in a pattern, such as a crossed pattern. This pattern could include two separate wires in different directions, two separate wires in parallel in the same direction, or more than two wires in either separate or the same direction. These wires could also be connected together with either a mechanical coupling or an electrically conductive coupling so that they maintain their geometry during the RF cutting process. The wires 240 may also be separate from the bag 230 and may be arranged in a pattern that allows the specimen 250 to be placed within the loops of the wires. This pattern would include routing the wires into the lumen 110 and coupled electrically to a connector that delivers the RF energy to the tissue specimen, or routing the wires to fixed positions near the opening of the bag so that the lumen 110 could be placed in proximity to the wires and attached to form an electrical coupling that delivers the RF energy to the tissue specimen. These wires would be detached from the coupling of the bag mechanically either with pre-tension applied prior to the cut, with the mechanical loading aided by the temperature increase during RF cutting, or other similar means. This may be aided with insufflation of the bag either through the trocar or within the device. In one embodiment, and as seen in FIG. 1, the wires 140 may comprise a shape similar to an egg-beater upon encapsulating the specimen 150.

It is also contemplated that the device 100 may also comprise a second embodiment. In one such second embodiment the outer lumen 110 may comprise only the wires 140 and the tissue specimen bag 130 may be introduced into the patient with a separate mechanism such as, but not limited to, a grasper and manually manipulated in place.

A tissue manipulator may be used in conjunction with the device 100 to place the tissue specimen 150 through an opening of the bag 130. Once the specimen 150 is located in the bag 130, a guide wire may be pulled or the wires 140 may be retracted to close the opening of the bag 130 and/or to also tighten the wires 140 around the specimen 150, capturing and securing the specimen against the wires 140. The opening of the bag 130 may then be retracted along the outer surface of the lumen 110 toward or outside of the access port in the patient. Additional embodiments may comprise a securing mechanism, such as, but not limited to, a non-conductive netting or wires around the specimen 150, an inflatable feature, or a band around the outer circumference of the specimen 150, and/or may comprise inserting a non-conductive extension from the distal end 120 of the device 100 into the tissue specimen 150 to hold and secure it in conjunction with the device 100. The device 100 may further comprise an "umbrella catcher" device to extend beyond the specimen 150 and when activated pulls back to capture it. Such a catcher may be operated through the introduction of a separate component such as, but not limited to, an inflatable "balloon bag" which may compress the specimen 150 against the device 100, through filling the cavity with a fluid to compress against the bag 130 and the specimen 150, or with the addition of features that can hold the specimen 150 against the device 100 such as, but not limited to, through hooks that are deployed into the tissue specimen 150 proximal the distal end 120 of the device 100. One particular method of inflating the bag would be to have a multi-layer bag with a sealed volume between the inner and outer layers. This volume would be directly accessed by a fitting that would either be attached to the body of the bag or with an extension of the bag to extend outside of the patient during use. This fitting could receive either a syringe, external air cylinder or hospital air connection to inflate the bag, thereby compressing the tissue as described above. The fitting may also be used in conjunction with a valve. The pressure could be adjusted with the valve or with a separate valve/manifold that is incorporated with the system outside of the patient. Inflation of the bag can also be an additional protection in the potential of elevated tissue temperatures being thermally conducted to surrounding structures or tissue due to the RF cutting effect as an insulating layer of air would be captured between the tissue specimen where the RF cutting is occurring and the tissue outside of the bag.

In one embodiment, the bag 130 may comprise a tab, hook or other feature which enables another instrument or tool to couple to a side of the bag 130 and place the bag 130 in a desired position within the patient's body. Such a feature may be adapted for use with larger specimens 150, for example. The tabs or other features may be located on the top, bottom or sides of the bag such that it can then be grasped by the user to more easily control the bag while placing the specimen within the bag. The tabs may also be used when pulling the bag either into the instrument end or through the patient incision, natural orifice, or trocar. These tabs may be color coded in order to aid in bag orientation identification. An additional self-expanding feature(s) located within the bag or within the bag opening may be integrated to aid in opening and accessing the bag during loading of the specimen. The self-expanding feature may be a ring or multi-pronged shape and composed of an elastomer, thermoplastic, or metal such as spring wire or Nitinol. It may also be an inflatable feature with addition of forced air or a sterile liquid. The feature may have an end that can be accessed or pulled in order to remove the self-expanding feature prior to segmentation or removal of the bag from the patient.

In at least one embodiment, the wires 140 may be used as the active electrode for the RF energy. The number of wires 140 in the device 100 may comprise from one wire to hundreds of wires, dependent on the interior volume of the lumen 110. The wires 140 may be either electrically connected to form one active electrode that will all be used simultaneously or may be electrically isolated from each other and used sequentially. These wires 140 may also be arranged in groups which are isolated from other groups of wires. In one such embodiment, the wires 140 may be adapted to cut serially rather than in parallel, with each group of wires cutting at a different time than the other groups of wires, although overlapping of cutting times may occur. It may also be advantageous to hold the specimen 150 together until the cutting of the specimen 150 is complete. Cutting in such a manner may create an "orange slice" effect of the specimen 150 or may create "rectangles" or other geometrical patterns as determined by the routing and spacing of the wires. The resulting geometry is important as related to the size of the opening used for removal. Methods to secure the tissue specimen during cutting can include, but are not limited to tightening the specimen bag 130 around the tissue specimen using mechanical force either applied by a mechanism incorporated into the device 100, aspiration of the air internal to the bag using a suction mechanism incorporated into the device 100 (i.e., hospital suction, a syringe, air cylinder, or other methods), or by using other holding features such as, but not limited to, a wire or band coupled to the specimen 150 around, for example, a middle cross-sectional area of the specimen 150, or by applying a force by hand.

Cutting the specimen 150 with the wires 140 may require rapid, low-temperature RF wire cutting based on a combination of mechanical and electrical energy. For example, as the mechanical force pulls the wires 140 through the tissue specimen 150, the electrical energy facilities separation of the tissue. The interaction and optimization of these separate cutting forces are adapted to minimizing cutting times and tissue temperatures. The cutting requires two phases of electrical energy delivery. First is initiation of the RF cutting. Second is sustaining the cutting while the wire 140 cuts through the tissue. The electrical energy is delivered through the exposed wire 140 in contact with the tissue. Without power density levels of greater than 1150 W/in$^2$, preferably above 1240 W/in$^2$, initiation of the RF cutting may be difficult due to the surface area of the exposed wire surface. Furthermore, such power levels may be difficult to deliver safely. As disclosed herein, several approaches may be used to overcome this challenge.

The wires 140 may comprise one or more exposure sections. For example, one or more sections of the wires 140 may comprise an electrically conductive path to the tissue in the area in which RF energy is applied to the tissue specimen 150 to perform the cutting. This exposure can range from the entire length of the wire 140 to small fixed length of the wire 140. Such sections may be created by adding insulation to the wire 140 at locations on the wire outside of the intended one or more exposure sections. The exposure section may also comprise variable exposure sections. For example, the device 100 may comprise a separate mechanism to retract and/or properly position the insulation along the wire prior to and/or during the cutting of the specimen 150 with the wires 140 occurs, allowing the section of the wires 140 exposed to and adapted to cut the specimen 150 to change either before or during use. This exposure may be completely uninsulated. Alternatively, the exposure section may comprise a coating that allows current to flow to the surface of the coating when a set of conditions are satisfied (i.e., a coating temperature, an active electrode voltage and/or energy delivery capability conditions are satisfied, etc.). The coating may also comprise a porous insulator that may allow a high current density energy to emit from the wire 140. Or, a selective removal of the insulation may occur in a pattern that allows a controlled surface area of the wire 140 to be in contact with the tissue specimen 150. In one embodiment, the insulation may be applied with a separate insulating jacket, a separate insulating component bonded to the wire or can be a coating applied directly to the wire. The coating properties may be used to either create the exposure size or to alter the cutting effect. In one embodiment, the coating is adjusted so that it is thicker to be more of an electrical insulator in areas where cutting is not intended. This change in thickness can be created by adjusting the process used to apply the coating, or with secondary operations including repeating the process over selected areas of the wire. In addition, the type of material can be adjusted to alter the cutting effect and the ability to re-initiate the RF energy after cutting is terminated. The coating, where intended, will be removed from the wire during cutting due to the localized rapid temperature increase resulting from the current conduction from the wire to the tissue. The ability of the material to withstand this localized temperature increase, the strength of the bond between the material and the wire and the thickness of the coating all can affect the rate at which the coating is removed. As the removal of the coating increases the contact area between the wire and the tissue, the impedance is reduced and the surface area of the active electrode increases resulting in a change in the electrical parameters. These parameters can be utilized to adjust or control the cutting effect. As an illustrative example, as the temperature capability of a material is increased, the rate of removal will reduce resulting in a slightly slower and more controlled cut. In addition, at the completion of the cut, more residual coating material will remain on the wire enabling a higher starting impedance which improves the probability of initiation of a second RF cutting application. Another method of controlling the electrical properties of the wire would be to use layering techniques in either the coating or the wire to alter the conductivity. This could be achieved by different types of coatings applied to a wire or with different types of conductive materials used to create the wire such as an inner conductive material enclosed within a second conductive material or any combination of solid or braided conductive materials enclosed within each other. The braided material can provide an improved conduction electrically and can also provide a higher tensile strength wire with a smaller overall diameter as well as provide a higher flexible wire to reduce the possibility of kinking.

The return electrode is an electrically conducting component that is placed in contact with the tissue specimen 150. It can either be a component that is located proximal to the bag 130 and wires 140 so that when the bag 130 and wires 140 are deployed the return electrode will be located near, or integrated with, the distal end 120 of the device and will also be in contact with the tissue specimen 150. In another embodiment, the return electrode may be coupled to the distal end of the lumen 110 in a fixed position. The return electrode is electrically isolated from the active wires 140 and is of sufficient size to minimize or eliminate cutting and/or reduce heat at the tissue return electrode site. The return electrode may comprise a circular, flat, or rounded disc located near a center of the device distal lumen 100 or can comprise a ring that surrounds the device distal lumen 100. The return electrode may be applied to the tissue with deployable contact areas located on the distal end of the device 100. These contact areas can normally be in a closed position prior to deployment of the bag and upon deployment extend outward beyond the distal end of the device and beyond the diameter of the lumen 110 in a pivoting motion. The resulting geometry has extensions surrounding the distal end opening that form contact points along a circumference in a plane above the distal end of the device lumen. The material of the extensions may be composed primarily of an insulator that can withstand a high temperature with a conductive layer located either in the inner surface and/or the most distal surface of the extension. Alternatively they may be composed of a metal that is partially coated with an electrically and thermally insulative material such that only the tissue is in contact with the conductive metal. The device 100 may be configured so that the active electrodes do not come in contact with the return electrode when the wires 140 have been retracted. For example, the wires 140 may be channeled away from the return electrode through the use of insulating features attached to or above the return electrode or surrounding the wires such as with small tubing or tubes that provides electrical insulation and that guides the wires and allows them to slide into the tubing while cutting, thereby insulating the return electrode from the wires 140. It is also contemplated that the return electrode may be electrically related from the distal end 120 of the device 110 to another location on the tissue specimen 150 when the cutting of the specimen 150 is complete (i.e., non-activated wires, feature added to the distal end of the inner bag surface, band surrounding the tissue, an electrode integrated to the non-conductive extension securing the tissue). The location of the return electrode can be changed during the sustaining cutting function to one of the locations described above and/or to locations on the bag to take advantage of the proximity of the wires as the cutting occurs to reduce the chance of the active electrodes coming into contact with the return electrode. One embodiment would be to apply an electrically conductive layer to the inside surface of the bag 130 such that when tension is applied to the bag against the device 100, electrical contact is made with the tissue specimen 150. This conductive layer would act as the return electrode and can be constructed in a geometrical pattern to separate the return from the wires 140. In addition, the bag could be constructed to have an additional layer of insulation applied over the electrically conductive layer to create a desirable geometry of electrically conductive areas within a larger insulation layer. These layers can be created with multiple process operations or by molding the electrical layer within the bag during manufacturing. In another embodiment the conductive elements on the bag may protrude from the bag surface to make contact with the tissue. In a related embodiment the return elements may be part of integrated inflatable features on the bag, which would help ensure contact of the return elements. The conductive elements can be composed of metal or other conductive polymer.

The terms active electrode or active electrodes as used herein may refer to the wires 140. It is further contemplated that the generator may also sense a change in impedance once the wires 140 near the return electrode upon retraction of the wires 140. When the change in impedance is detected, power may be adjusted or shut off to the wire in which a change in impedance is detected. In a separate embodiment the return can be a band around the specimen that plays a dual role of return and holding the specimen during cutting.

Mechanical cutting forces may be applied to the wire to initiate or otherwise enable cutting. For example, tension, dynamic loading, slicing (repeated lateral motion of wire against the specimen 150), or vibratory forces may be used and may further comprise a benefit of lowering the amount of total energy needed to cut through the specimen 150. Mechanical cutting forces may also reduce the temperature proximal to the device 100, as the use of mechanical forces may initially embeds the wire into the tissue specimen 150 prior to the use of RF energy to continue the cutting of the specimen 150. Mechanical loading also reduces the time and power required for cutting. Mechanical loads used with RF wire cutting should be greater than 40 psi on the load-bearing portion of the wire 140 (typically half of the wire surface area). Loads lower than 40 psi may be insufficient to provide low temperature RF wire cutting. Prior to the cut, the wires may require tension to be applied to decouple the wires from the bag and to bring the tissue specimen 150 into direct contact with the distal end of the device 110. This tension helps secure the tissue specimen 150 and helps align the wire geometry to the tissue prior to beginning the cut. This tension should be in the range of 40 to 100 psi over the surface of the wire. This tension range may be lower than 40 psi if other means are used to secure the specimen. As the RF is applied, this tension should be maintained during the entirety of the cut to provide the most efficient cutting effect which will lead to a lower tissue temperature, allow for lower power settings from the generator and maintain the cutting geometry through the tissue specimen.

As the tension of the wires toward the device 100 increases, the pressure applied to the wires at the distal end of the lumen 110 increases resulting in a higher potential frictional force that must be overcome between the wires and instrument distal end to perform the cutting. Methods to reduce this include having a material at the distal end of the lumen, particularly at the inner-diameter surface that can withstand higher temperatures and provides a lubricious surface finish, such as PTFE or similar materials. Another embodiment that may reduce the frictional force between the wires and instrument end would be to have a feature in the distal end that allows the wires to travel below the contact point of the tissue at the lumen 110. This feature could be one or more cut-outs that provides an area that the wires can travel that may naturally align with the wires due to the location or can be "guided" with other components of the device such as the insulation tubing previously mentioned. This feature can also be created with the deployable extensions described in earlier that allows the wires to travel between the contact areas of the extensions.

Integration of this device with an electromechanical system, such as a surgical robot or electromechanical arm, can further enable use of mechanically aided cutting. Electromechanical arms can be used to apply the mechanical action without risk of operator fatigue or the need for a separate mechanical actuator. Another electromechanical arm may also be used to help hold the bag 130 in a desired position, view or otherwise visualize the outside of the bag 130, or aid in tracking or removing the specimen 130. Once the specimen has been segmented, an additional compressive load may be applied to the bag that orients or positions the resulting segments for easier removal of either the segments or the entire bag.

Along with wire tension, cutting the specimen 150 is often dependent on two additional functions: the initiation of energy and the sustaining of the energy during the cut. The initiation of energy is achieved when an arcing of the RF energy begin to vaporize the tissue proximal the wires 140 while sustaining the energy comprises continuing to deliver energy to the wires 140 in order to maintain the arcing during the travel of the active electrode during the cutting of the tissue 150. Initiating cutting typically requires more energy than sustaining the cut. This is because before RF energy is applied to the wires, the specimen 150 comprises electrical impedance characteristics that are much lower in comparison to tissue that has already received RF energy. The impedance range for a typical tissue specimen 150 with no RF energy applied to the specimen 150 will comprise from about thirty to about one hundred Ohms for uninsulated wire, depending on the geometry/surface area of the active electrode exposed to the specimen 150 as well as the material of the wire 140. By contrast, the impedance range of the specimen 150 where RF energy has already been applied to the tissue (during the sustaining cycle) can be from about sixty to about one thousand Ohms. This change in the tissue impedance occurs due to the change in hydration of the tissue (desiccation) as a result of the localized heating, the separation of tissue structures, and the creation of steam due to the vaporization of tissue cells. It is desirable to operate the electrode in a constant power range of the electrosurgical generator. For example in the case of the Valleylab Force FX and Force Triad generators the constant power range is between about 64 ohms and about 4096 ohms.

Typical electrosurgical generators are designed to have maximum power transfer at a rated load of commonly 300 to 500 Ohms for monopolar cut modes. Power transfer to load impedances below this range can be limited by the design of the generator, particularly if a current limit is designed into the system. As a result, the lower impedance which occurs attempting to initiate the cutting effect can operate in the current limited region and therefore limit the voltage necessary to begin the cutting effect. Using Bipolar modes on these generators results in an output designed for a lower impedance which can improve the power transfer. However, these Bipolar modes are typically limited for use below 100 W. This power range may limit the size of the exposure on the wires 140, both for initiation and sustaining the cut.

There are two commonly used approaches to overcome the low impedance initiation effects. In the first, the impedance effect may be overcome by controlling the exposure of a single wire loop and by applying a pulsed energy in a non-continuous waveform, such as a Blended cut. This is typical of the Lina Loop system. In the second, conductive fluid is introduced into the area around the device to ensure a conductive path. In this application, this effect is overcome by controlling the dimensions of the loop exposure and proximity to the return path on the device and/or by applying pulsed energy in a non-continuous waveform such as a Blended cut waveform, with an amplitude decay of the pulse envelope. This is typical of the Olympus Bipolar Resection system.

Other methods to offset the low impedance effect can be to limit the exposure to match the available range of the RF energy source or to use a higher output RF energy source optimized for the lower impedance range. Limiting the exposure will have the negative effect of limiting the size of the resulting cut with a particular wire. Increasing the RF energy source is limited by international safety standards to a maximum of 400 W and may increase concerns of leakage or unintended current paths due to the large amount of current required by this approach.

The device 100 uses one or more of several embodiments to initiate the cutting effect. In one embodiment, a coating on the wire 140 increases the tissue-electrode interface impedance to allow the generator to create the voltage necessary to initiate the cutting effect. This coating can be a high temperature, high dielectric strength insulator such as PTFE, PFA, FEP, Silicone, or polyimide (Kapton) which have use temperatures at or above 320 degrees F. The resulting impedance observed by the generator will comprise on the order of several hundred to tens of thousands of ohms prior to initiation and reduce to about 50 and up to 1000 ohms during the cutting process, depending on the wire surface contact area with the tissue specimen 150, coating material properties, thickness of coating, wire material, and specimen composition. As the RF energy is applied through the wire 140, variations in the thickness and structure of the coating creates very small areas of variation of impedance between the electrode and tissue. When the voltage applied to the wire reaches the required potential to overcome the dielectric withstand of a localized lower impedance portion of the coating, an arc is produced through this area of insulation creating a micro void in the coating and the initiation of the cutting effect is achieved. Given the relationship between power delivery and electrode surface area, an optimal wire power density is desired. For example for PTFE-coated 304 stainless steel wire, power densities greater than 1240 W/in$^2$ provides rapid initiation and low temperature cutting. Ideally the power densities are greater than 1340 Watts/square inch to better adapt to harder tissues such as uterine fibroids. This embodiment adds little cost to the device 100 while withstanding multiple cut initiations before breaking down.

Therefore, if power is halted to the wire electrode for any reason, the cut can be reinitiated. As the number of wires increases, or the size of the tissue specimen becomes larger, it requires more energy to perform the sustaining function of the cutting cycle. This is due to the lower impedance observed by the generator as the surface area of the active electrode increases. As earlier described, a natural limit of a generator output into low impedances will result in a limit of power that can be delivered to the tissue. A means to improve this would be to create a generator output that can provide a higher voltage during the initiation function with a lower current limit and to transition to an output that can provide a higher current output during the sustaining function. This transition can be performed either electronically or with a change in the software control. The transition point is determined by the initial rise in current that accompanies the initiation effect. For this embodiment, the generator must be designed to naturally output the largest power demand but the limits applied with either electronic or software control can maintain the maximum output power to within the 400 W dictated by the safety standards. Another method that may be used to improve the energy delivery capability would be to use multiple generators that provide RF energy to a subset of active electrodes and/or return electrodes. This will allow a lower power setting for each generator to deliver the total power required to perform the sustaining function into low impedance tissue. Another alternate method is to rapidly pulse the energy delivered during one or both of the initiation or cutting cycles such that the overall average power is minimized.

An insulative high temperature coating on a wire electrode may be beneficial in other surgical applications outside of specimen removal where a wire 140 is used to cut through tissue. Examples of other wire cutting applications include wire loops for amputating the uterus from the cervix (Lina Loop by Lina Medical), Lletz loops, bipolar resection loops, and polypectomy loops. Advantages may include initiating cutting while in contact with the tissue, less power needed to initiate cutting, lower resulting temperatures that reduce the chance of damage to adjacent anatomical structures, and less smoke to cloud visibility to the user.

Other ways of creating the increased impedance for initiation can be a NTC or negative temperature coefficient material or a variable exposure that begins at a small exposure length and is increased after activation and ether a wire 140 that allows delivery of a higher impedance fluid or air pressure to increase the localized active electrode-tissue interface impedance. The increased impedance may also be created by adding a component proximal to the exposure that mechanically expands or contracts with temperature to create a gap and results in an increase in impedance with lower temperatures. In addition, a lower temperature coating can be utilized so that once the wire 140 reaches a melting point of the coating, the coating breaks down, allowing initiation to occur. With such an approach, the wire 140 may only be used once to initiate a cut. Coatings can be applied either continuously or in a pattern that simulates a continuous number of small exposures or creates an effective higher impedance over a longer exposure length.

In one embodiment, a colorant or dye may be added to the outside of a wire 140 or wire coating to mark the sample before or during cutting. A recent study showed that morcellated uterine samples are more difficult to accurately assess pathology than non-morcellated specimens. The dye marks left on the tissue, in combination with more regular cuts, may be beneficial to a pathologist who is performing an histologic assessment.

In addition to a coating, the generator may employ one or more of several embodiments to initiate the cutting effect. The generator can add a pulsed high voltage output that is ac coupled or integrated as part of the generator output in order to provide a short duration higher voltage to initiate the RF activation. The generator can also provide a high current to desiccate the tissue thereby increasing the tissue impedance resulting in higher voltage or can vary the delivery of the RF energy intermittently to increase the energy delivered to the tissue specimen 150 for a shorter duration followed by a lower continuous energy level for sustaining the energy. As the tissue impedance is very low at the beginning of initiation and increases after the cutting effect begins, the power required for these two phases differs. For initiation without a wire coating, a high power setting is required to provide the voltage required to produce the arc with high current delivery into the low impedance tissue. After the initiation during the sustaining phase, the impedance increases requiring much less current and therefore less power. The generator can sense the current to determine when initiation begins. Prior to initiation, the current will be high and a transition of the current to a much lower level indicates the beginning of the cutting effect. The generator can use this information to provide a higher power setting during initiation and reduce the power to a lower sustaining power setting. The generator can also keep track of the time in the initiation phase as provide other means to initiating the cutting effect such as increasing the power to a predetermined setting or limit or applying pulsed output until the current transition is observed.

Another method of initiating the cutting effect is to pre-treat the tissue specimen 150 to increase the impedance at the tissue-wire interface by desiccation of the tissue and/or increase the temperature of the localized tissue. This can be done by pre-heating the localized tissue by applying heated air near the wire or by using wires 140 designed with the inclusion of materials that are temperature sensitive to current, such as Nichrome, where the high initial current needed before initiation increases the wire 140 to pre-treat the tissue to allow the RF energy to begin the cutting and the lower current necessary to sustain the energy allows the RF energy to continue the cutting. This can also be achieved by using a magnetic coated or magnetic composition wire 140 with a higher frequency continuous waveform added to the fundamental RF waveform. This higher frequency waveform will cause the magnetic material to increase in temperature. The high frequency waveform can be applied at the beginning of RF activation and removed when the lower frequency RF output begins the initiation as determined by the current delivery. The high frequency waveform can be in the MHz to tens of MHz range or can be higher as determined by the geometric properties of the active electrode and the magnetic material properties.

Another embodiment utilizes two closely spaced, substantially parallel wires 140 in which one wire 140 operates as the active electrode and the other wire 140 operates as the return. The closely spaced wires 140 reduce the distance between active and return resulting in faster heating and cutting of the tissue specimen 150.

The generator may be set at the nominal power setting to perform the cutting effect. The range of power settings required are determined by the exposure size, or surface area between the tissue specimen 150 and wire 140, and are typically in the range of 60 to 280 Watts. The RF energy is applied in a bipolar fashion with the current being contained within the tissue specimen and not intended to be delivered to the adjacent tissue structures. Containment of the specimen 150 in the insulative bag 130 adds additional electrical isolation of the specimen 130 from the rest of the patient. The generator may provide adjustments of amplitude or duty cycle of the output using an algorithm based on the current delivery and impedance observed during initiation and sustaining the cut.

As mentioned earlier, the amount of mechanical load applied is also important for a reliable and fast cutting. To ensure that the optimal load of 40-100 psi (half the wire surface area which is applying the load on the tissue) is applied, it is preferred that the amount of load is controlled by the instrument rather than rely on the user to guess an appropriate load. In one embodiment a spring load is applied to the wire ends. The spring may be activated by the user in order to apply the load by manually extending a "trigger" that preloads the spring, by squeezing a handle with a mechanism that stretches a spring, or an approach easily conceived by those skilled in the art. In another embodiment, the spring in a relaxed state provides separation of two electrical contacts that complete the circuit for RF delivery to the wires 140. While the spring is in the relaxed state, these electrical contacts do not have an electrical coupling and the RF energy cannot be delivered to the wires 140. The spring is selected so that when the desired optimal load of 40-100 psi is applied to the wire ends it compresses such that the two electrical contacts come in contact with each other producing an electrical coupling and thereby delivering RF energy to the wires 140. The spring and spacing of the contacts can be designed to ensure that the minimum load is applied before RF energy is delivered, and can also be designed such that applying a load above the desired value can extend the contacts beyond each other removing the electrical coupling.

In another embodiment, the user can supply the force needed to perform the cutting and a sensor that can measure the applied force can be included to provide information to a control mechanism, such as a microprocessor, FPGA, analog control circuit, or other similar control device, such that the RF energy is only applied when the force is within the acceptable range of 40-100 psi.

After completion of the tissue reduction, the device 100 may be removed by releasing any connections of the bag 130 that may remain to the device 100. If the bag was not exteriorized for cutting, the device 100 may use a guide wire or wires to ensure the bag 130 can be located externally from the patient through the access port. These guide wires may aide in pulling the opening of the bag 130 through the port to aide in removal of tissue segments. In another embodiment, a clip is applied to the bag using a grasper or other manipulation tool to seal off the bag opening. The tissue segments inside the contained bag may be manipulated within and along the length of the bag to create a long and narrow series of tissue segments. The bag containing these tissue segments can be manipulated toward the access point, either the vagina for gynecological procedures, or other the access port such as the umbilicus for SILS procedures, or mini-laparotomy for other types of minimally invasive procedures. Small features can be included in the bag to grab the tissue, such as small "hooks", to aid in distributing the tissue along the length of the bag during manipulation.

Removal of the tissue segments may be achieved by inserting a tissue grasper into the opening of the bag 130, grasping segments and removing them through the port contained within the bag 130. To aid in location and grasping the segments, tension applied by pulling the exposed portion of the bag can be used to pull the segments together, or insufflation of the bag can be used to extend the bag into the cavity and create more space for movement and manipulation of the segments. To aid in tissue grasping, a method of maintaining the port opening may be required. This expansion may be achieved by using currently available products, such as a wound retractor. Other embodiments may use a retraction method that is accomplished with features integrated into the specimen bag, or may be a separate instrument. Integrated bag expansion option embodiments may include a means to expand the bag just prior to and/or just after the point where the bag exits the port opening. This integrated expansion may be accomplished by a mechanical means, such as an expanding wire or an elastic ring, or by insufflated pockets within the bag. Embodiments for separate retraction instruments may include a semi-rigid cuff to mechanically expand the port opening. The external cuff could comprise a rough surface texture in order to aid in maintaining the cuff in the inserted position. The cuff inside surface could include a lubricious coating in order to aid in tissue segment removal. The cuff instrument position could also be maintained with the help of other features, such as a ballooning feature on the exterior, distal end of the cuff which, when inflated, would prevent the cuff from becoming dislodged. Other embodiments for a separate retraction instrument may include a collapsible ring or spiral shaped device that could be collapsed for ease of insertion. Once in place the collapsed shape could be released and allowed to spring back to its relaxed configuration, thus expanding the natural size and/or shape of the port opening. In addition, an endoscope may be inserted with a light source for better visualization to aide grasping. Depending on the size of the resulting tissue segments related to the access port size, the trocar may be removed prior to tissue fragment removal to assist in removal of large segments. Other embodiments may be the addition of non-conductive, serrated (hook-like) strips that are temporarily attached to the inside lining of the bag. These strips can be used in lieu of, or in addition to a tissue grasper. Once tissue segmentation is complete—these non-conductive strips can be pulled sequentially from the bag 130, thus aiding in the expeditious removal of the specimen segments. Alternatively the bag may have a narrower end or bottom that collects the segments into a smaller area for retrieval. In another embodiment a grasper with an integrated camera may be used to aid in seeing and grabbing the segments from the bag during removal. Other alternatives include an instrument with a barbed or hooked end that grab the tissue segments while the user pulls the instrument towards the bag opening or a suction device, lighted or not lighted, that can be placed in the bag and "grab" segments using air suction.

Thermal protection of the body cavity and adjacent tissue structures outside of the specimen bag 130 may occur. The tissue specimen bag 130 may include one or more features to reduce or eliminate thermal conduction from the tissue specimen 150, before, during and after reduction. These measures are: an insulating material lining the bag 130, mechanical features such as dimples or spacers that are molded or applied to the bag 130 to create a separation of the tissue 150 from the bag surface, a multiple layer bag 130 with positive air pressure or fluid applied between the layers once filled with the tissue to provide insulation and spacing between the two layers, non-conductive fluid or air circulated within the bag 130 around the tissue specimen 150, fluid circulated within the body cavity around the specimen bag 130, a Venturi cooling system with multiple ports to create a Venturi effect, a heat pipe, adding heat-sinking material around the specimen bag 130 such as wet surgical towels or thermally protective material inserted either before the device 100 is introduced or just prior to cutting. Other measures to control the thermal conduction is controlling the energy to apply the minimum amount needed to perform the cutting, particularly in the sustaining energy phase of cutting with modulating the power amplitude or pulsing the output. Thermal protection may also be needed for the return electrode, and as the wires exit the tissue such as in the distal end of the handle or introducer. As mentioned earlier, tension on the wires 140 may "bury" the wires 140 in the tissue specimen such as to reduce temperatures seen by adjacent structures. Increasing the mechanical force reduces the time and the power needed to cut thereby reducing the temperature.

Other means to provide thermal protection are to incorporate thermally sensitive features into the bag 130, such as thermocouples, thermistors or a thermally sensitive lining within the bag 130 to provide a visual indication of hot spots. The generator can modulate the output based on the feedback from these sensors. The temperature can also be inferred by monitoring the electrical parameters and calculating the energy being delivered and estimating the resulting temperature. A known threshold can be used to compare the actual calculated energy for a period of time verses the typical energy delivered for a specimen. This can be used to control the output by modulating the RF energy delivered to the tissue.

The device 100 and method described herein may be used in other procedures where large volume tissue specimens are to be removed, such as lung lobectomies, spleen removal, kidney removal or other procedures where a more minimally invasive approach is desired.

After the specimen has been loaded into the bag & before RF energy is applied, it is desirable to pretension the entire wire assembly 140 in order to secure the specimen with respect to the wires. This wire pretension will also embed the wires into the specimen prior to the application of RF energy—thus minimizing the potential spread of elevated temperatures outside of the intended specimen. This wire pre-tensioning can be accomplished with an independent mechanism, or combined with the mechanism used for mechanical tension during the specimen cutting process. Pretension values need to stay below the ultimate tensile value of the wires to which the pretension mechanism is attached. Ideal pretension values occur in a range that mechanically embeds the wires prior to cutting, and balances the progression of the wire movement through the specimen while getting the optimal cutting effect (low-temperatures to the surrounding specimen) from the RF energy. This pretension should be in the range of 40-100 psi for each wire. This tension range may be lower than 40 psi if other means are used to secure the specimen.

In some device configurations multiple mechanical pulls of subsets of wires may be needed to accomplish the required specimen segmentation prior to removal from the body. This pulling mechanism can be the repeated motion of one mechanism being attached to a different subset of wires, or a dedicated mechanical mechanism can be used for each wire subset. In one embodiment, a plurality of constant-force springs can be used to apply tension to a subset of wires such that these subsets can be pulled sequentially during the cutting process. Each constant-force spring spool can be electrified sequentially in order to active the RF cutting process in a sequential order.

The device will use a cable to electrically connect to an electrosurgical generator. The connection can be made using a standard 3-pin monopolar active connector and a 2 pin monopolar return connector, a standard two pin vessel sealing connector for generators that provide vessel sealing with the appropriate energy delivery capability or with a custom electrical connector designed for the tissue removal system. The electrical connection is electrically connected through the cabling to inside the lumen. There the electrical connection can be connected to a common terminal of a switch that will change positions to align with the set of wires intended to perform the next cut. This can be accomplished mechanically by the user rotating a collar or control to the desired position, can be initially set to the first position as part of the manufacturing process and advanced automatically by the pulling mechanism within the device, can be automatically advanced using an electromechanical drive component such as a step motor, can be connected via transistor, relay or other switching device driven by a logic circuit or microprocessor control, or can be selected by application of force or advancement of the pull mechanism to perform the cut. This connection can be provided through the mechanical structure of the pull mechanism (spring, rod, etc.), can be a separate component that acts like a "buss" bar located on the lumen with a wiper located on the pull mechanism to complete the electrical connection, or with a wire running along the pull mechanism that is pulled in conjunction during cutting. The device may only allow one set of wires to be electrified at any given time. The return will be connected to the appropriate return electrode, either in the bag, distal end of the device or other location, and will be isolated by separation and insulated materials to avoid a short circuit or to reduce electrical leakage current.

The active electrode wires can be secured to the pull mechanism in a variety of ways including a custom connector that provide a mechanical side load to capture the wires, a connection provided with a screw that applies and captures the wire ends, a crimp that holds the wire ends that is integrated into the pull mechanism end or secured or captured into a design feature in the pull mechanism end, a solder or a welding operation, addition of a fixed geometry on the wire such as a sphere or cutout that is placed in a mating feature on the pull mechanism that locks it in place or a clip that is designed into the pull mechanism that grabs into the wire such that it is easily inserted but cannot be easily removed.

The device may include features to ensure proper operation and reduce the likelihood of inadvertent RF thermal damage. One of these features may be to disallow RF energy from being applied to the wires 140 until the bag is deployed, the wires pre-tensioned and the opening of the bag exteriorized and tensioned along the outer surface of the lumen. This can be accomplished by having force sensors integrated into the pull mechanism and bag guide wires to measure pre-tensioning that provides information to a control to enable the RF energy after the sequence has been successfully completed or with an in line spring that controls separated electrical contacts as previously described. It may also be accomplished by having mechanical features located along the lumen of the device and corresponding mechanical features on the pull mechanism and bag guide wires such that these mechanical features are in alignment mechanism, such as a microprocessor, FPGA, analog control circuit, or other similar control device, when the wires and bag are pre-tensioned at the minimum to maximum load range. This alignment may produce an electrical coupling such that a low voltage interrogation signal can be used as a control signal to enable the RF energy to be applied. Another feature may be to have a predefined sequence to apply the RF energy to successive wire pairs. This may be accomplished by have a rotating knob that is electrically coupled to the RF energy common connection and rotating to preset positions make the connection to the corresponding pull mechanism and/or electrical coupling path for the corresponding wire set. This could also accomplished with a rotating mechanism that advances the RF common connection as described above where the advancement of the RF energy common is performed by a mechanical feature in the pull mechanism design at the proximal end of the travel that forces the RF energy common to the next location. This may also be accomplished by an electromechanical device, such as a stepper motor, that can automatically advance the RF energy common to the next location. Another feature may be to include temperature sensors within the device in the bag or lumen of the device. These temperature sensors can be thermistors, thermocouples or other semiconductors that use electrical signals to infer temperature. These sensors can be measures by a control mechanism, such as a microprocessor, FPGA, analog control circuit, or other similar control device, such that the control device can disable or limit the RF energy output, such as amplitude or pulse modulation, to maintain proper temperature ranges within the device. They can also be used with an analog circuit that can act as a resettable fusible link to disable RF energy when the temperature exceeds a preset threshold. Another feature would be to ensure that all metal parts that are in proximity of electrical coupling paths, such as constant-force springs, pull rods, or connectors, are electrically isolated either with insulating materials or applied coatings. This will reduce the possibility of unintended electrical coupling from the active electrode wire set to other wire sets. Another features would be to have an electrical circuit that can perform an open or short circuit check prior and/or during RF energy application. This detection can be performed with an electrical circuit that can be used to determine if RF energy should be applied or terminated. Another feature may be to include information within the electrical plug that is connected to the electrosurgical generator. This information could be used to set the power and mode values, could be used to verify that the generator is set to the proper power and mode values or could be used to provide other information to the generator about the device to give performance values that enhance the safety and efficacy of the system. This information can be labeled on the outside of the plug or provided with an RFID label attached to the plug, embedded into an RFID chip or electrical memory device (i.e., EEPROM, flash memory, microprocessor, or other memory device) within the plug, or could be a passive component, such as resistor, that can be measured to provide an index to a pre-defined table containing the information within the generator.

In some embodiments, identification features previously described may be incorporated into connectors that interface the wires 140 or sets of wires intended to cut at the same time. These features allow the device 100 to adjust the power levels if differing exposures were desired for different areas of the tissue specimen, such as a shorter exposure at the periphery allowing a lower power setting to perform the same cutting effect or for more precise power adjustment for different bag sizes and shapes resulting in different wire lengths.

Turning now to FIGS. 3-30, details of how to make and use the device 100 and various embodiments are now described. For the purpose of this document, unless otherwise stated, the terms "wire" and "electrode" may be used interchangeably. Where a distinction is required, a "wire" is generally intended to refer to a conductive portion of an electrode. For example, in FIG. 30, feature 1400 may be referred to as an electrode 1400 or more generally as a wire 1400. In FIG. 30, the electrode or wire 1400 is illustrated with a conductive wire 1406.

Figure 3:
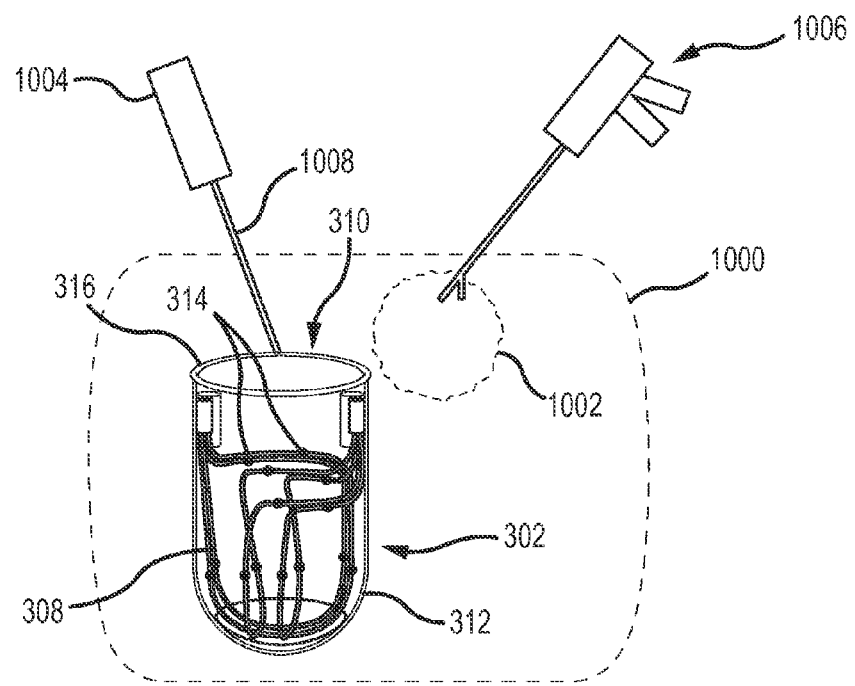
FIG. 3 illustrates an exemplary retrieval bag deployed in a patient.

Illustrated in FIG. 3 is a retrieval bag 302 according to some embodiments, deployed inside a cavity 1000 of a patient. The retrieval bag 302 is shaped and sized so as to receive a tissue specimen 1002 that is being surgically removed from the cavity 1000. Those of skill in the art will understand how to select the appropriate sizing of the retrieval bag 302 in relation to the particular tissue specimen 1002 being removed.

In the embodiment shown, the retrieval bag 302 has a container 312 with an entry 310, and a plurality of electrodes 308 disposed in the container 312 in a manner that will be described in further detail in subsequent portions of this disclosure. The container 312 may be flexible and deployable through a standard surgical tube, such as a cannula or lumen, as is known in the art. In some embodiments, a fastener 314 or a plurality of fasteners 314 may be provided to temporarily or permanently fasten the electrodes 308 to the container 312 in a desired configuration.

A spring-biased ring 316 may be provided at the entry 310 of the retrieval bag 302 to ease the opening of the retrieval bag 302; however, those of skill in the art will understand that this is not necessary to practice the invention. In some embodiments, the container 312 and the fasteners 314 are configured to be deployed through a tube, such as through a deployment instrument 1004, into the cavity 1000 and allowed to spring into place.

After the retrieval bag 302 is in place, a grasper 1006 or any means known in the art may be provided to manipulate the specimen 1002 into the retrieval bag 302 prior to removal from the patient. Those of skill in the art will understand how the surgical team might loosen the specimen 1002 and move it into the retrieval bag 302.

Figure 4:
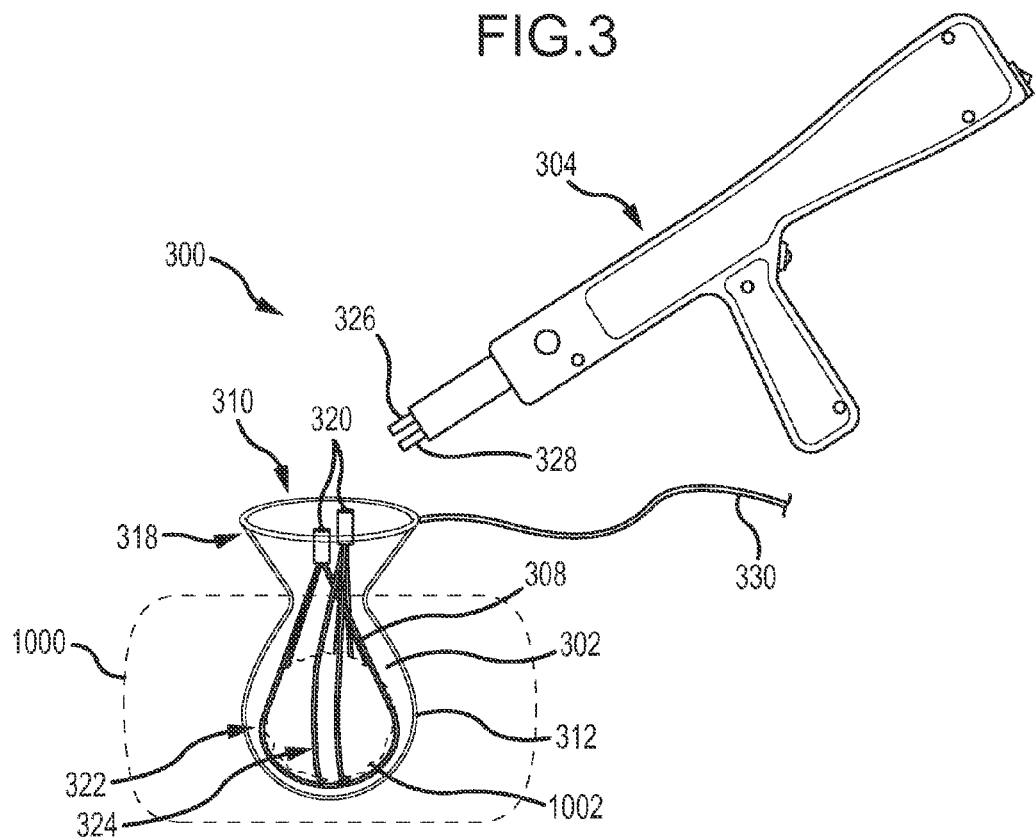
FIG. 4 illustrates the retrieval bag of FIG. 3 in an exteriorized state.

Turning now to FIG. 4, a proximal portion 318 of the retrieval bag 302 and respective proximal portions 320 of the electrodes 308 may be exteriorized, that is, pulled out of the cavity 1000 such that a surgeon can access the proximal portion 318 of the retrieval bag 302 and the proximal portions 320 of the electrodes.

In some embodiments, the proximal portions 320 of the electrodes 308 are pre-crimped to facilitate attachment to an actuator 304 although those of skill in the art will understand that this feature is not necessary.

In some embodiments, a first set 322 of electrodes 308 is crimped or otherwise coupled at the proximal portions 320 to facilitate attachment to a first actuator rod 326. Similarly, a second set 324 of electrodes 308 may be crimped or otherwise coupled at the proximal portions 320 to facilitate attachment to a second actuator rod 328. Further details of the attachment will be described in subsequent portions of this disclosure, although those of skill in the art will readily envision any number of means for attaching the electrodes 308 to the actuator 304, all of which are contemplated.

Figure 5:
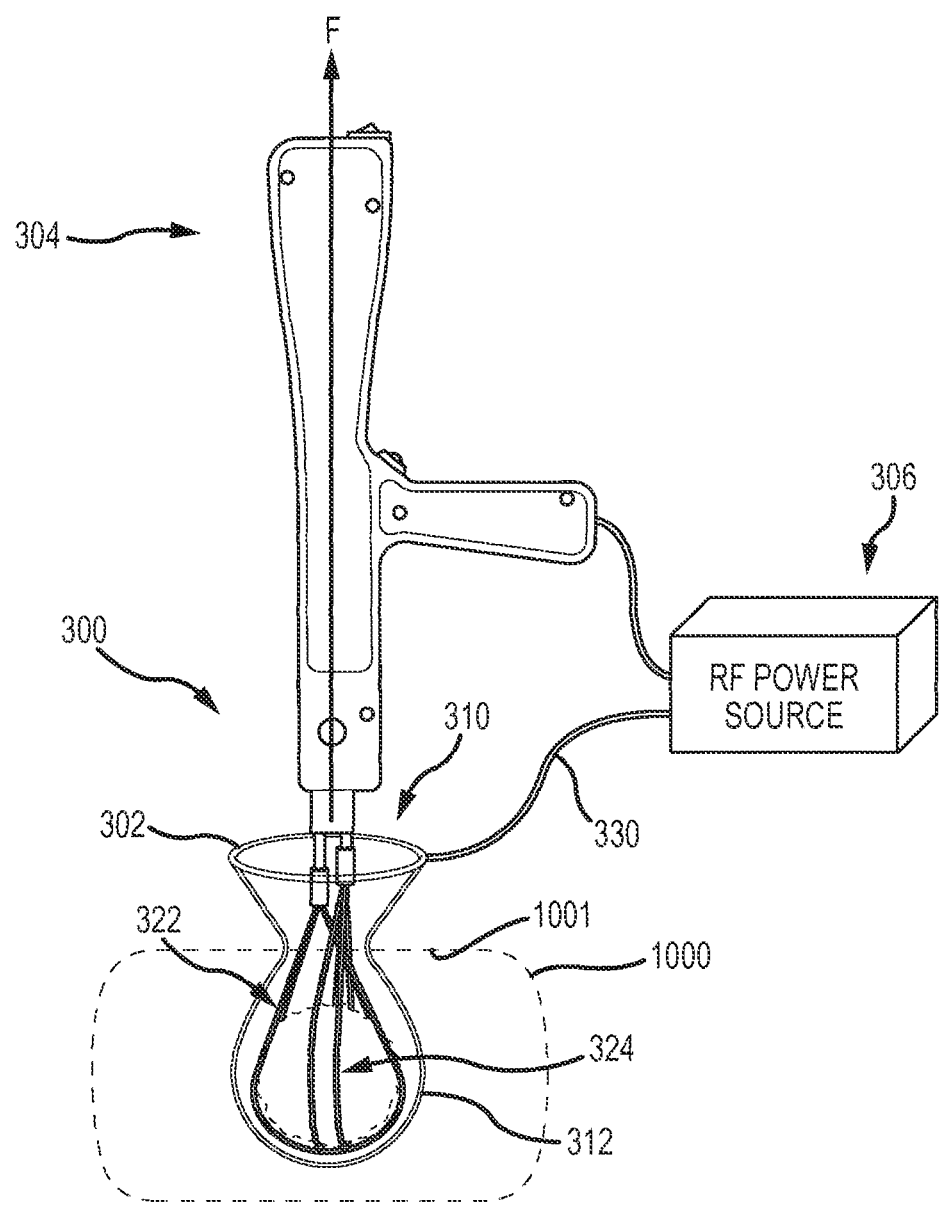
FIG. 5 illustrates the exteriorized retrieval bag of FIG. 4 with the actuator and generator attached.

In some embodiments, and as illustrated in FIG. 5, a proximal force F may be applied to the electrodes 308 to initiate and/or maintain a tissue segmentation operation. Those of skill in the art will understand that an opposing force is necessary to maintain the actuator 304 and retrieval bag 302 in a stable position.

In some embodiments, portions of the retrieval bag 302 containing the specimen 1002 and electrodes 308 are configured to not contact the interior wall 1001 of the cavity 1000. In some embodiments, a distal insertion tube 538 (see e.g. FIG. 11) is provided, against which the specimen 1002 may abut while the electrodes 140, 308 are being pulled through the specimen 1002. In some embodiments, an additional thermal barrier (not shown) is provided in a wall of the retrieval bag 302 or on an exterior surface of the retrieval bag 302 so that any contact with the cavity 1000 will be protected from thermal damage. The thermal barrier may include a thermally insulative layer 1304 or a feature that can be inflated with air or a fluid (see e.g. FIG. 26). In some embodiments, the surgeon may use a laparoscopic camera to visually ensure that no contact is being made with the interior body cavity 1000.

Turning now to FIG. 5, in some embodiments, after the exteriorizing of the retrieval bag 302, an actuator 304 may be coupled to the proximal portions 320 of the electrodes 308. As will be understood by those skilled in the art, a generator 306, such as a radio frequency (RF) power source may be coupled to the actuator 304, and a return electrode 330 may be coupled to the retrieval bag 302, if one was not previously provided. The tissue removal device 300 is illustrated in FIG. 5 in a ready-state for tissue segmentation.

Figure 8:
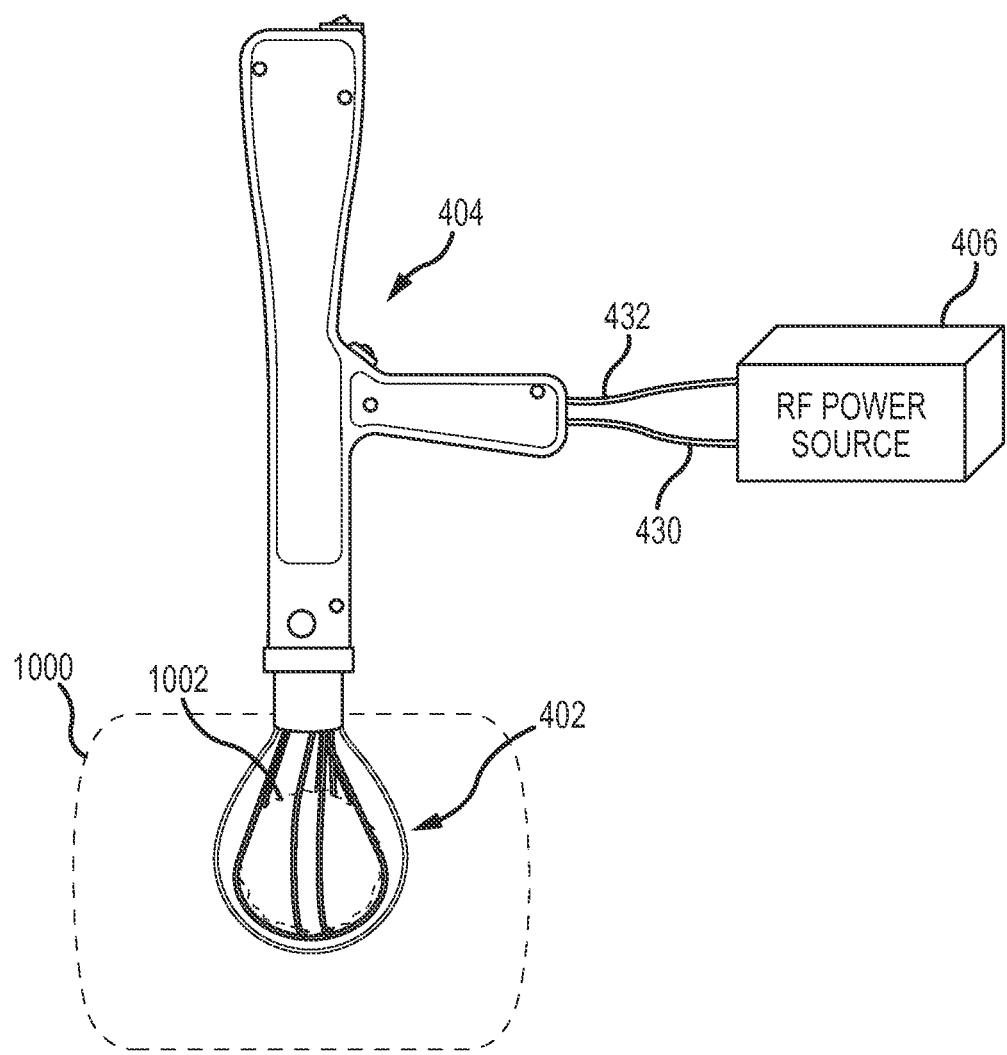
FIG. 8 illustrates the device of FIG. 7 with a generator attached.

Turning now to FIG. 6, an embodiment of the tissue removal device 400 is now described in detail. As illustrated in FIGS. 6-8, in some embodiments, the tissue removal device 400 includes a retrieval bag 402 and actuator 404 that are coupled or assembled together prior to insertion into the cavity 1000 and/or placement of the specimen 1002 inside the retrieval bag 402. For example, the tissue removal device 400 may have a retrieval bag 402 and an electrode 408 or electrodes 408 that are biased to expand upon deployment inside the cavity 1000, or remain expanded upon being forcibly expanded by, for example, a grasper 1006, such that the retrieval bag 402 and the electrode(s) 408 provide a receiving space 434 for a specimen 1002. The retrieval bag 402 may have an entry 410 that is generally to a side of the retrieval bag 402 as illustrated, such that transverse movement of the specimen 1002 allows the specimen 1002 to be placed inside the retrieval bag 402. In some embodiments, the entry 410 may be a longitudinal slit in the retrieval bag that may be pulled open by a biasing effect of the electrodes 408, forcibly opened as a user forces the electrodes 408 into a spaced-apart configuration, and/or a user pushing the specimen 1002 into the entry 410. The entry 410 may be biased towards a closed configuration, and/or the entry 410 may be sealable using means known to those of skill in the art. In some embodiments, actuation of the actuator 404 may cause the electrodes 408 to move towards each other and thereby sealing the entry 410 and/or causing opposing portions of the entry 410 to overlap to effectuate a barrier between the specimen 1002 and the cavity 1000. In some embodiments, causing the electrodes 408 to apply a proximal force F on the specimen 1002 may cause the retrieval bag 402 and entry 410 to draw into the actuator 404 to effect a closure of the entry 410 or a barrier between the specimen 1002 and the cavity 1002. In some embodiments, the actuator 404 is attached to the retrieval bag 402 prior to deployment into the cavity 1000.

Turning to FIG. 7, the entry 410 of the retrieval bag 402 may be exteriorized as the actuator 404 applies a proximal force F to the electrodes 408. The proximal force F may also substantially simultaneously cause the retrieval bag 402 and electrodes 408 to contract or move inwardly to surround the specimen 1002 and effectuate a desired surrounding of the specimen 1002 and/or a desired electrode configuration or pattern relative to the specimen 1002. In some embodiments, a mechanical operation such as manipulation of a switch or lever may be performed so as to effectuate a retraction of the electrodes 408 and proximal force F on the tissue specimen 1002.

In some embodiments, and as illustrated in FIG. 8, after the retrieval bag 402 is exteriorized, a generator 406 may be attached to the actuator 404 so as to allow energy to be applied to the electrodes 408. Attaching the generator 406 may include coupling a power source line 432 and a return electrode 430 in a manner known to those skilled in the art.

Figure 9:
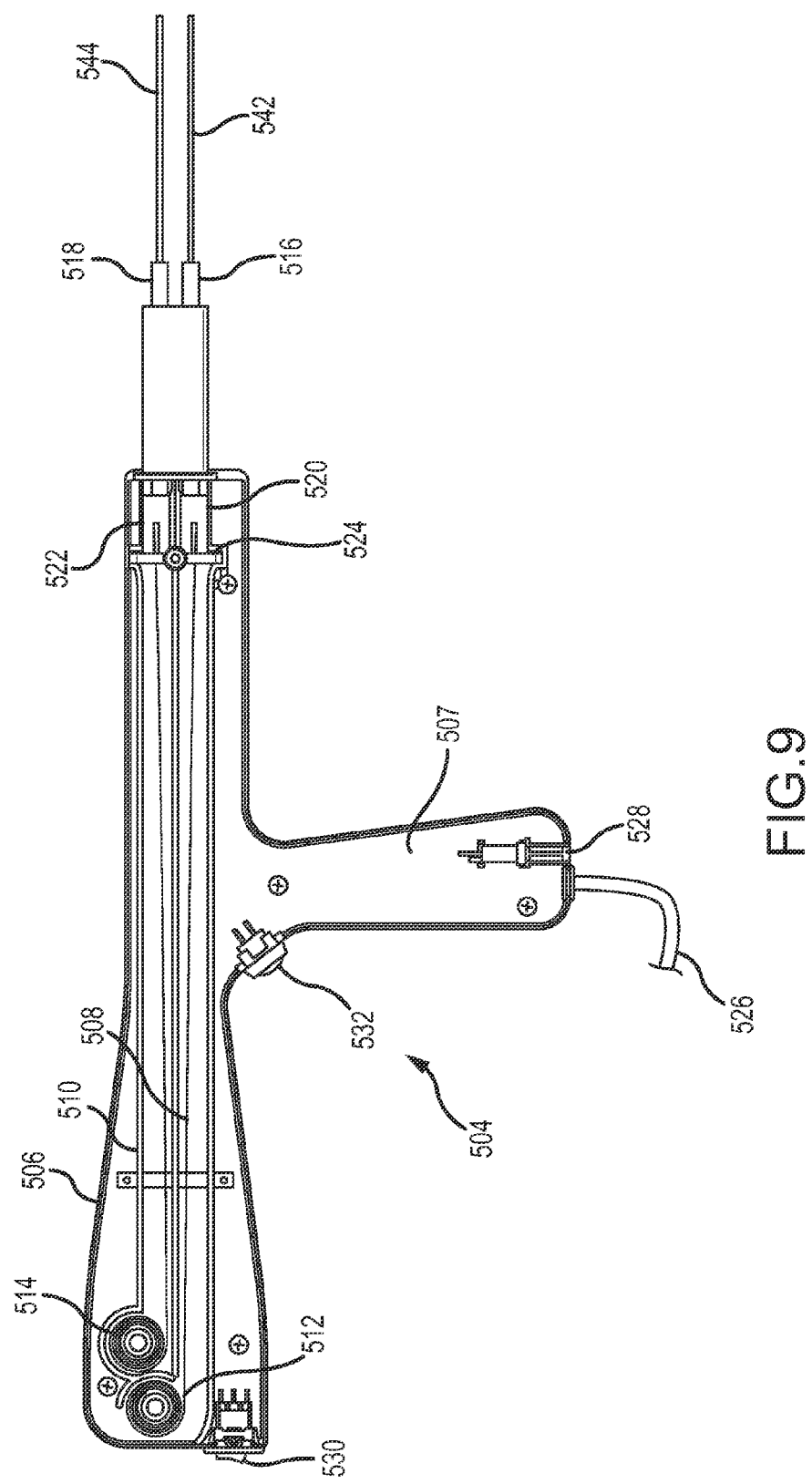
FIG. 9 illustrates a side view of components of an exemplary actuator prior to an actuation.
Figure 10:
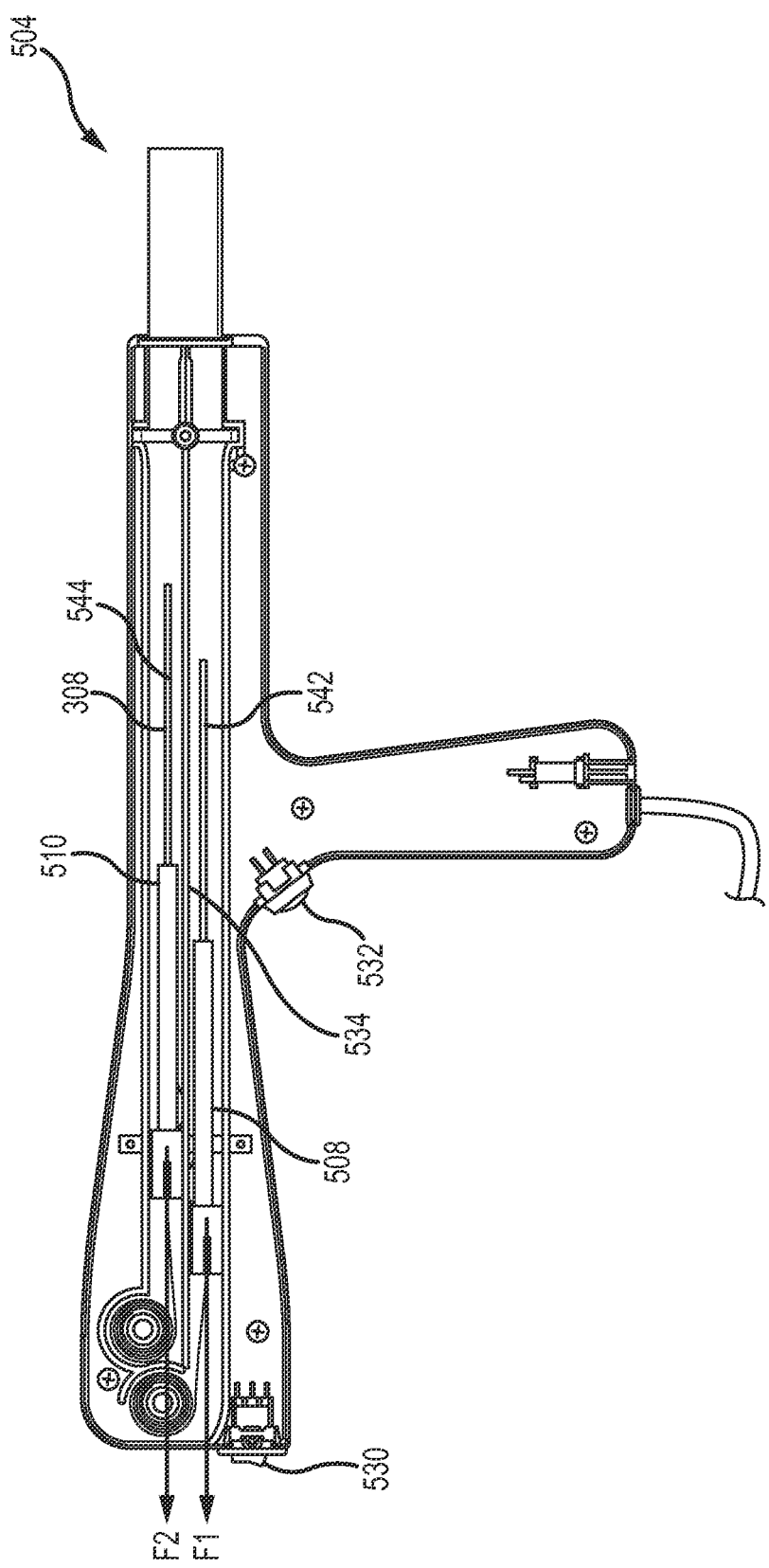
FIG. 10 illustrates a side view of the actuator in FIG. 9 in a post-actuation state.

Turning now to FIGS. 9-10, details of an exemplary actuator 504 according to some embodiments are now described in further detail. As illustrated, the actuator 504 may have a housing 506 supporting one or more pull assemblies 508, 510. The housing 506 may have a handle 507 for assisting the user in controlling a position of the actuator 504. Although the handle 507 is illustrated as substantially perpendicular to the rest of the housing 506, those skilled in the art will understand that a handle 507 may be provided in any relation suitable, and that a handle 507 is not necessary for the actuator 504 to function.

As illustrated in FIG. 10, a first pull assembly 508 may be configured to apply a first force F1 on a specimen prior to and/or during a segmentation procedure, such as by way of a first electrode 542 or first crimped set of electrodes 542. A second pull assembly 510 may be configured to apply a second force F2 on the specimen prior to and/or during the segmentation procedure, such as by way of a second electrode 544 or second crimped set of electrodes 544. The first force F1 may be applied or commenced prior to commencing application of the second force F2. The first force F1 may be completed prior to commencing application of the second force F2. The first force F1 may continue through at least a portion of an application of the second force F2. The magnitude of the first force F1 and the second force F2 may be controlled and varied in a manner discussed in other sections of this disclosure. That is, the forces F1, F2 may effect proximal forces on the specimen 1002 that vary during a segmentation procedure.

The first pull assembly 508 may include a first spring 512 coupled to a first connector rod 516 by way of a first spring-connector rod block 520. In some embodiments, the first spring 512 (and/or a second spring 514) may be a linear spring. The first connector rod 516 may be coupled or configured to couple to a first electrode 542 or a first crimped set of electrodes 544 (see also FIGS. 4, 7). Similarly, the second pull assembly 510 may include a second spring 514 coupled to a second connector rod 518 by way of a second spring-connector rod block 522. The second connector rod 518 may be coupled or configured to couple to a second electrode 544 or a second crimped set of electrodes 544.

Continuing with FIGS. 9-10, the actuator 504 may include a spring holder or spring pretension latch 524 to maintain the spring(s) 512, 514 tensioned prior to a segmentation procedure.

The actuator 504 may also include a power cable 526 or power cable connector and a return connector 528 for coupling the actuator 504 to a power source, such as a generator 306, 406 as illustrated in FIGS. 5 and 8. A return connector 528 may be provided to allow an electrical return path through the actuator as illustrated in FIG. 8, or a return path may be provided independent of the actuator 504 as illustrated in FIG. 5.

Continuing with FIGS. 9-10, a power toggle 530 may be provided to select or turn on one or more of the first or second electrode sets 322, 324 in the order that they are to be activated by the actuator 504, while a power activation button 532 may be provided to allow the user to determine when to apply energy to the electrodes 542, 544. In some embodiments, power may be applied to the electrodes 542, 544 by way of a power strip 534. In some embodiments, the power strip 534 may be fixed and insulated within the housing 506 so as to provide a separating wall between components of the first and second pull assemblies 508, 510. In some embodiments, the power strip 534 may be aligned or attached to a spring separation wall 535 (see e.g. FIG. 11). In some embodiments, power may be applied to the spring 512 with a spring contact located on a wall of the actuator housing 506, for example at the proximal end of the device, near the spring coil. In some embodiments, the spring contact may be integrated with a spring housing design used to capture the spring. In some embodiments, power is applied to the electrodes 542, 544 using a flexible cable or set of wires that can movably extend into the device 504 during the cutting process. This allows the power delivery to be decoupled from the mechanical actuation components for cutting.

Figure 11:
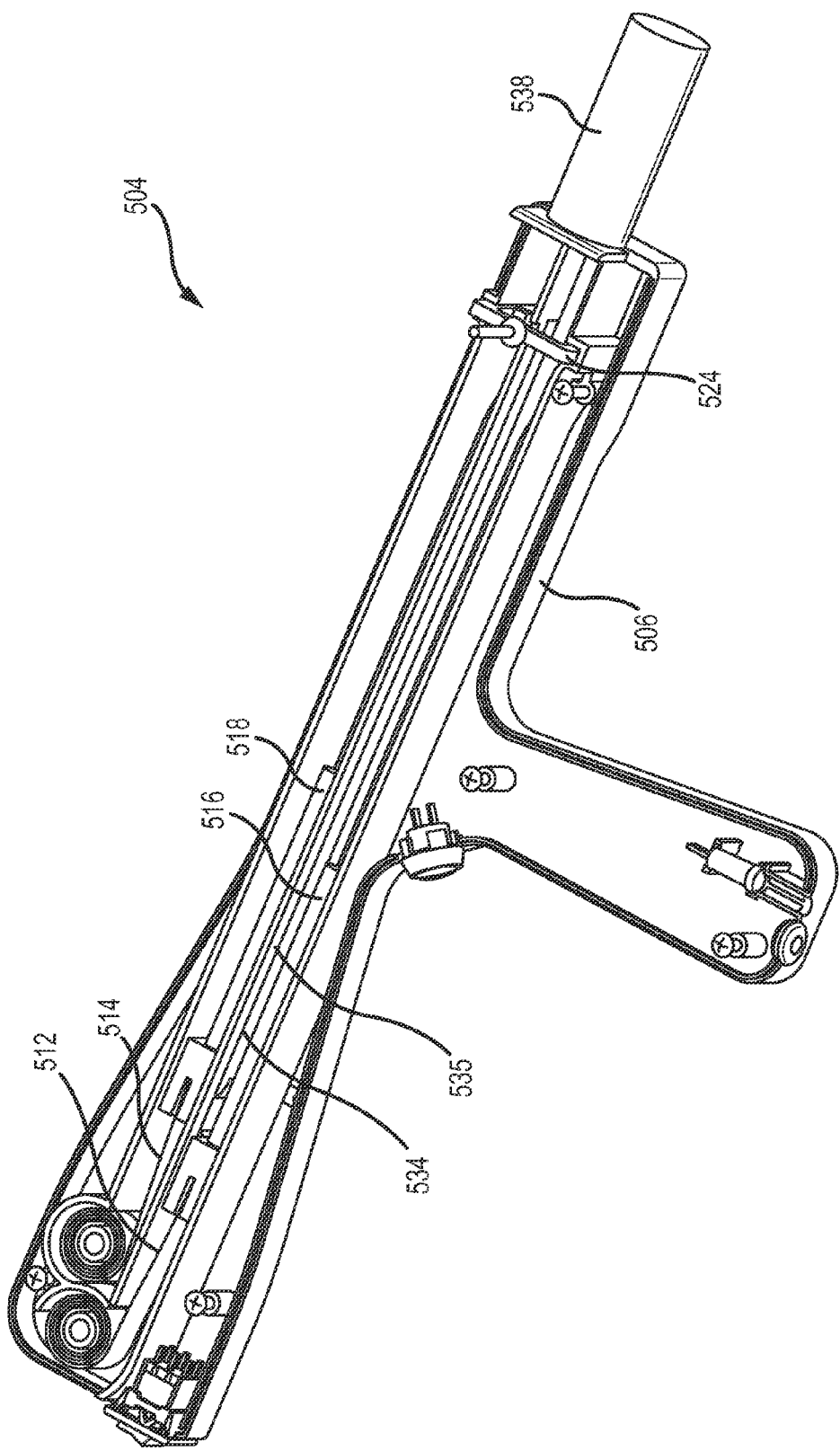
FIG. 11 illustrates a perspective view of some details of the actuator in FIG. 9.
Figure 12:
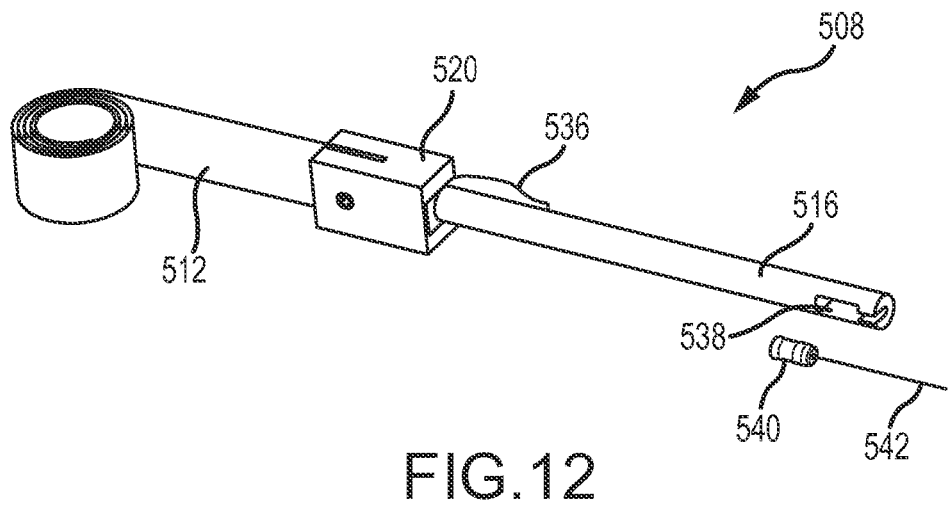
FIG. 12 illustrates a perspective view of an exemplary spring connector rod block assembly prior to wire attachment.
Figure 13:
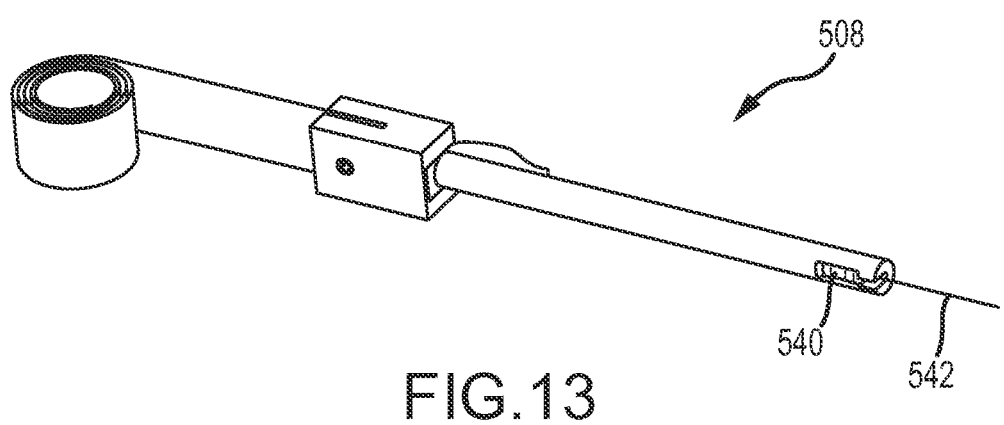
FIG. 13 illustrates a perspective view of the spring connector rod block assembly of FIG. 12 post wire attachment.

Turning now to FIGS. 11-13, mechanical and electrical details of some embodiments of the actuator 504 are now further described. As illustrated, a pre-tension latch 524 may be provided. This pretension latch 524 maintains the tensioning springs 512, 514 in an extended position. Depressing the pretension latch 524 unlocks the pre-tension lockout and allows all tensioning springs 512, 514 to retract the electrodes 308, and pull or otherwise contain the specimen 1002 tightly against the distal end of the tissue removal device 300, 400. Those skilled in the art will understand that numerous means for pre-tensioning may be provided, all of which are contemplated in this disclosure, including, but not limited to: a separate pretension mechanism which, when activated, retracts the segmentation actuators away from the specimen to be segmented—thus pre-tensioning the specimen. In some embodiments, springs 512,514 are responsive to a mechanism to pre-tension the specimen 1002. The springs 512, 514 may wind up at their respective mounting locations, or increase the path length, or route, the electrodes 542, 544 need to travel for their retraction. In some embodiments, portions of the tissue removal device 300, 400 are disposable. In some embodiments, the actuator 304, 404, 504 is disposable. In some embodiments, the actuator 304, 404, 504 is re-usable. In the case of a re-usable actuator 304, 404, 504, the user might redeploy the springs 512, 514 while using the pre-tension latch 524 to maintain the extended position as done initially.

With particular reference to FIGS. 12-13, the first pull assembly 508 is described in detail. As previously described, the first pull assembly 508 may have a first spring 512 coupled to a first connector rod 516, such as, for example only, by way of a spring-connector rod block 520. The block 520 may provide a means for coupling a first electrode 542 or first electrode set to the first spring 512, such as by way of attaching a first connector rod 516 to the first spring 512. The block 520 or portions of the block 520 may include an electrically conductive material so that attaching the first connector rod 516 may provide an electrical coupling between the first electrode 542, the connector rod 516, and the spring 512. In some embodiments, the block 520 may include an electrically insulating material to isolate the connector rod 516 and spring 512. In some embodiments, a power contact 536 may be provided by or coupled to the block 520 so as to allow energy, such as RF energy, to be applied to the specimen 1002 through the connector rod 516. The power contact 536 may be electrically isolated from the first spring 512. In some embodiments, RF energy may be applied to the spring 512 directly or indirectly, resulting in an electrical connection from the spring 512 through the block 520 and the connector rod 516 to the wires or electrodes 104, 308 and specimen 1002.

Continuing with FIG. 11, a distal insertion tube 538 may be provided to allow the actuator 504 to be inserted into a laparoscopic opening, and the length of the tube 538 is such that with the tube 538 fully inserted into the patient, the specimen 1002 and electrodes 308 or wires 140 will remain out of contact with the interior of the cavity 1000, which may be the abdominal or thoracic wall. The distal end of the insertion tube 538 may be rounded, and/or include a lubricious material to facilitate passage of the electrodes 308, 140 between the insertion tube 538 and the specimen 1002. In some embodiments, the distal end of the insertion tube 538 may have openings or be composed of a compliant material to facilitate wire movement. The proper instrument insertion length may be dictated by the instrument size proximal to the distal insertion tube. The distal insertion tube 538 may also have an inflatable feature, for example, on the proximal end near the actuator 504, that sits between the specimen 1002 and the inside cavity wall 1001 to further prevent the wires or electrodes from contacting the patient's body wall during retraction of the wires 140. In some embodiments, an additional thermal barrier (not shown) is provided in a wall of the retrieval bag 302 or on an exterior surface of the retrieval bag 302 so that any contact with the cavity 1000 will be protected from thermal damage. The thermal barrier may include a thermally insulative layer 1304 or a feature that can be inflated with air or a fluid (see e.g. FIG. 26). In some embodiments, the surgeon may use a laparoscopic camera to visually ensure that no contact is being made with the interior body cavity 1000.

Continuing with FIGS. 12-13, and as illustrated, for embodiments that require the user to make a connection of the electrodes 542, 544 at the distal end of the connector rod 516, a receiving space or slot 538 may be provided to receive a crimp sleeve 540 of an electrode 542 or a first set of crimped electrodes. The slot 538 may be shaped with a flange to enable the first spring 512 to apply a first force F1 on a first electrode 542 or a first crimped set of electrodes. Those of skill in the art will understand from the figures that the second pull assembly 510 may include the same or similar components for enabling the second pull assembly 510 to apply a second force F2.

Other means of connecting the electrodes 140, 308 to the actuator 504 other than a crimp are contemplated in this disclosure. One example includes terminating the electrodes 308 into a single-pin or multi-pin connector that is mated or configured to mate with a corresponding connector in the actuator 504. Another example includes using a hook that is placed into a feature of the connector rod to maintain the electrodes 308 coupled to the connector rod while under tension. Another example includes passing the electrode ends either individually or grouped together past a spring or hinged feature internal to the connecting rod, with this spring or hinged feature grasping the side of the electrode 308 and holding it securely when a removal force is applied.

Figure 14:
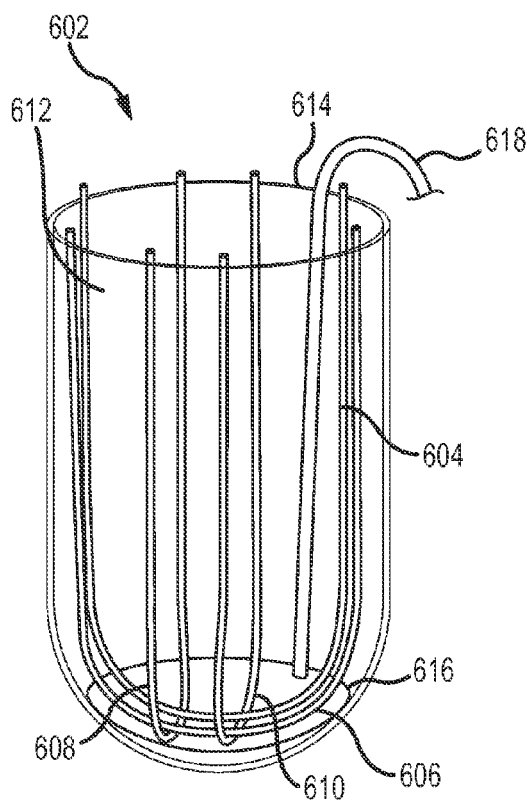
FIG. 14 illustrates a perspective view of an exemplary retrieval bag prior to a wire retraction.
Figure 16:
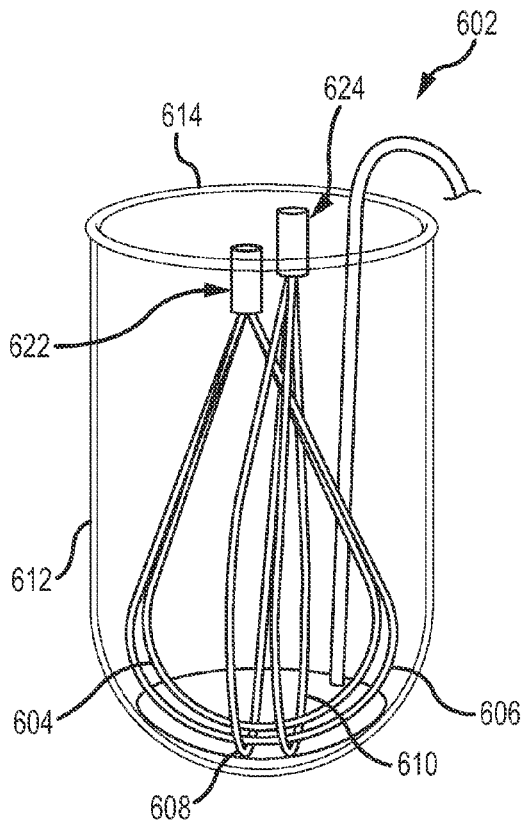
FIG. 16 illustrates a perspective view of the bag of FIG. 14 in a partially-retracted state.
Figure 15:
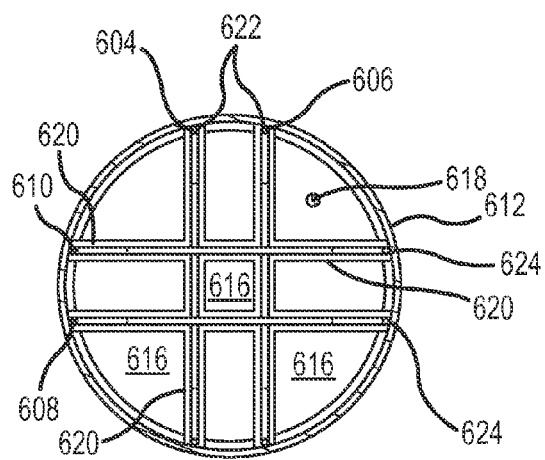
FIG. 15 illustrates a top section view of the bag of FIG. 14.

Turning now to FIGS. 14-16, an exemplary electrode arrangement is now described in detail. As illustrated, a retrieval bag 602 may be provided with a container 612 having an entry 614 and a plurality of electrodes assembled thereon; here, first, second, third, and fourth electrodes 604, 606, 608, 610 may be provided to segment the specimen 1002 into about nine segments, although it will be understood that more or less electrodes may be provided and that, even where four electrodes are provided, the specimen 1002 may affect the resulting shape and quantity of segments. A return 616 such as a return patch and a return cable 618 may be provided in a manner understood by those skilled in the art.

In some embodiments, the retrieval bag 602 may have an outer or first layer, such as a container 612 made of a plastic, polyvinyl, nylon, polyurethane, or any other bio-compatible insulating material suitable for use in a live patient. Coupled to or as a second layer in the container 612 may be a return 616. The return 616 may be a copper foil or mesh, or any other highly conductive material suitable for use in a live patient, coupled to a return cable 618 for transmitting energy from the patient. The return cable 618, while illustrated as being inside the container 612, may be coupled to the return 616 in any manner suitable for an efficient and safe transfer of energy, such as, being within the layers of the container 612 that are distal of the container entry 614, or sitting partially on the outside of the container 612 to keep the return cable 618 out of the way during specimen loading. The return cable 618 may be attached to the return 616 by soldering the return cable 618 to the return 616, mechanical contact applied by layering the return cable 618 and the return 616 together during manufacturing of the bag 602, adhering the return cable 618 to the return 616 using conducting epoxy or similar materials, and/or by forming the return 616 and return cable 618 from a single continuous foil or mesh.

Continuing with FIG. 15, interior of the return 616 or as a third layer may be a protective insulating material, such as a barrier 620 between the electrode(s) 604, 606, 608, 610 and the return 612. Those skilled in the art will recognize that, for specimen segmentation to occur, the specimen 1002 must be in contact with both the return 612 and the electrode(s) 604, 606, 608, 610, and that the return 612 cannot contact the electrode(s) 604, 606, 608, 610 directly. The barrier 620 is therefore an insulating layer between the return 612 and the electrode(s) 604, 606, 608, 610, and may be made of any material suitable for providing an insulating effect.

Those skilled in the art will also understand that the number of layers of the bag construction may be as few as one, two, or three, with components described above being attached to the interior surface of that layer or container 312 and may be greater than three, depending on the embodiment, and that components of the retrieval bag 602 illustrated in FIGS. 14-16 should be sized and suitably flexible so as to compress within an insertion tool prior to expansion within the cavity 1000.

Continuing with FIG. 16, the retrieval bag 602 may include a container 612 with an entry 614 that is biased to open upon deployment into the cavity 1000, or inflatable to an open configuration to allow the specimen 1002 to be placed into the retrieval bag 602. The electrodes may also be crimped together into a first electrode set 622 having first and second electrodes 604, 606 and a second electrode set 624 having third and fourth electrodes 608, 610. The first and second electrode sets 622, 624 may be coupled to pull assemblies 508, 510 respectively, as previously described herein.

The electrodes 604, 606, 608, 610 may be temporarily attached to the container 612 such that application of a proximal force F, F1, F2 may cause the electrodes 604, 606, 608, 610 to detach from the container 612. Means for attachment may include, but are not limited to, heat staking, stitching, glue adhesive, or other fastening means.

With simultaneous reference to FIGS. 15-16, the electrodes 604, 606, 608, 610 may be positioned or configured such that a first electrode set 622, 604, 606 may be activated to effect a first segmentation operation, while a second electrode set 624, 608, 610 may be activated to effect a second segmentation operation. The first segmentation operation may be completed prior to initiation of the second segmentation operation in some embodiments. In some embodiments, the second segmentation operation is commenced prior to completion of the first segmentation operation. In some embodiments, the second segmentation operation is commenced substantially contemporaneously with the first segmentation operation.

In some embodiments, an insulating layer (not shown) is provided between a first and second electrode 604, 606, 608, 610 so as to prevent premature transfer of energy to the second electrode and/or maintain a set power density for each electrode 604, 606, 608, 610. The insulating layer may include an additional low temperature temporary coating, an additional serrated bag feature, or other various methods. In addition to electrically isolating the electrodes 604, 606, 608, 610, the insulation also provides a mechanical barrier to reduce the chance of electrode breakage.

Figure 17:
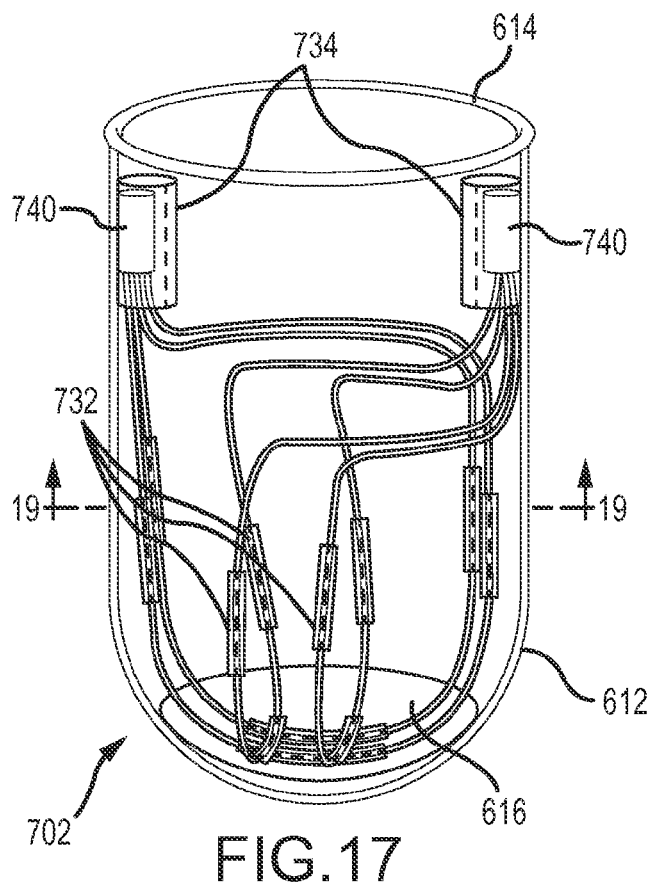
FIG. 17 illustrates a perspective view of another exemplary retrieval bag.
Figure 18:
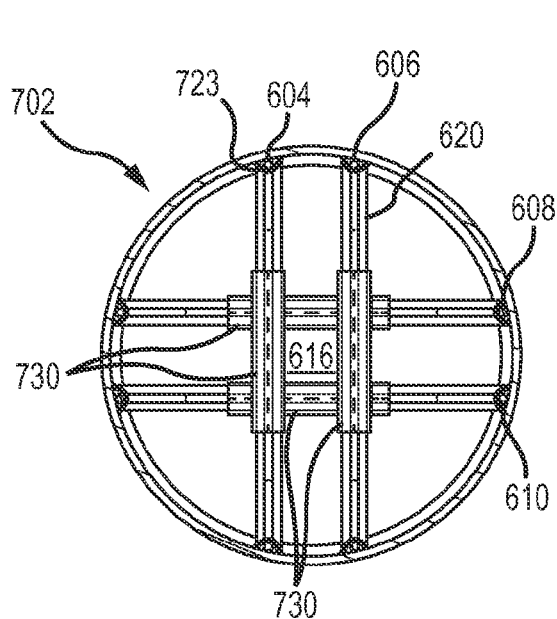
FIG. 18 illustrates a top section view of the bag of FIG. 17.
Figure 19:
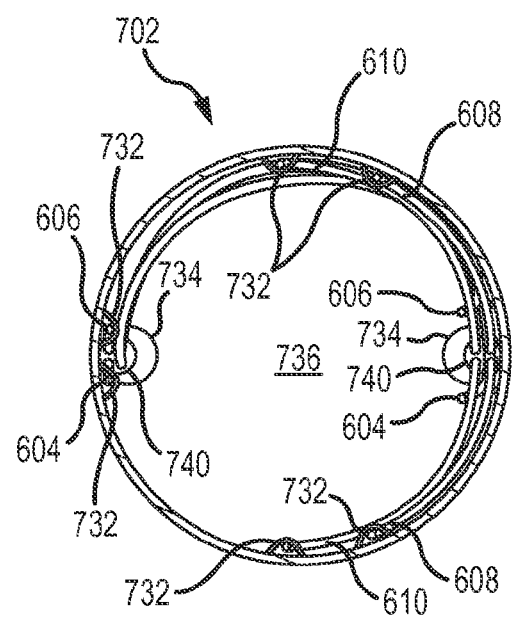
FIG. 19 illustrates a top cross section of the bag of FIG. 17.

Turning now to FIGS. 17-19, another embodiment of the retrieval bag 702 is now described in detail. To temporarily hold the electrode(s) 604, 606, 608, 610 in place prior to placement of a specimen 1002 inside the retrieval bag 702, one or more fasteners 730, 732, 734 may be provided. The fasteners 730, 732, 734 may be temporary, and include serrated or tear-away sleeves that hold the electrode(s) 604, 606, 608, 610 in place. In some embodiments, and as illustrated in FIG. 18, a first set of temporary fasteners 730 may couple a plurality of electrodes 604, 606, 608, 610 in a patterned configuration relative to a return 616 prior to a segmentation operation to maintain proper electrode spacing and to ensure the electrodes 604, 606, 608, 610 do not contact and/or short to the return 616.

As illustrated in FIG. 19, in some embodiments, a second set of temporary fasteners 732 may hold a plurality of electrodes 604, 606, 608, 610 in a pre-collection configuration, wherein the pre-collection configuration has an arrangement of the electrodes 604, 606, 608, 610 that provides an open receiving space 736 for a specimen. Another set of fasteners 724 which may be a third set of temporary fasteners, may temporarily or permanently couple the ends, which may be crimped ends 740 of one or more electrode sets 622, 624, near the bag entry 614.

In some embodiments, a first set of temporary fasteners 730 are selected to require a different pulling force to separate from the container 612 than is required to pull a second set of temporary fasteners 732 from the container 612. In some examples, the second set of temporary fasteners 732 may provide a relatively loose attachment to a side of the retrieval bag 702, such that the electrodes 604, 606, 608, 610 may be moved around or relative to the specimen 1002 after the specimen 1002 is collected in the retrieval bag 702 without causing the electrodes 604, 606, 608, 610 to tear through or break away from the first set of temporary fasteners 730 before the surgeon is ready to begin the segmentation procedure. In some embodiments, the third set of fasteners 734 may be temporary, and/or may require a detaching force that is greater than the detaching force required of the first and second sets of temporary fasteners 730, 732. The fasteners 734 may hold the electrode ends, crimps or other connectors out of the way and near the entry 614 during specimen loading. This allows the user to access and connect the electrodes to the actuator 504 from outside the patient after the entry 614 is exteriorized.

It should be noted that, although the return 616 is illustrated at a bottom portion of the retrieval bag 702, those skilled in the art will understand that the return 616 may be placed in other suitable regions of the retrieval bag 702, so long as the return 616 is placed in contact with the specimen 1002 and not in contact with the exposure of the electrodes

604, 606, 608, 610. It should also be understood that the retrieval bag 702 may have other features as described and illustrated with respect to other embodiments of the retrieval bag 602 previously and subsequently described.

Figure 20:
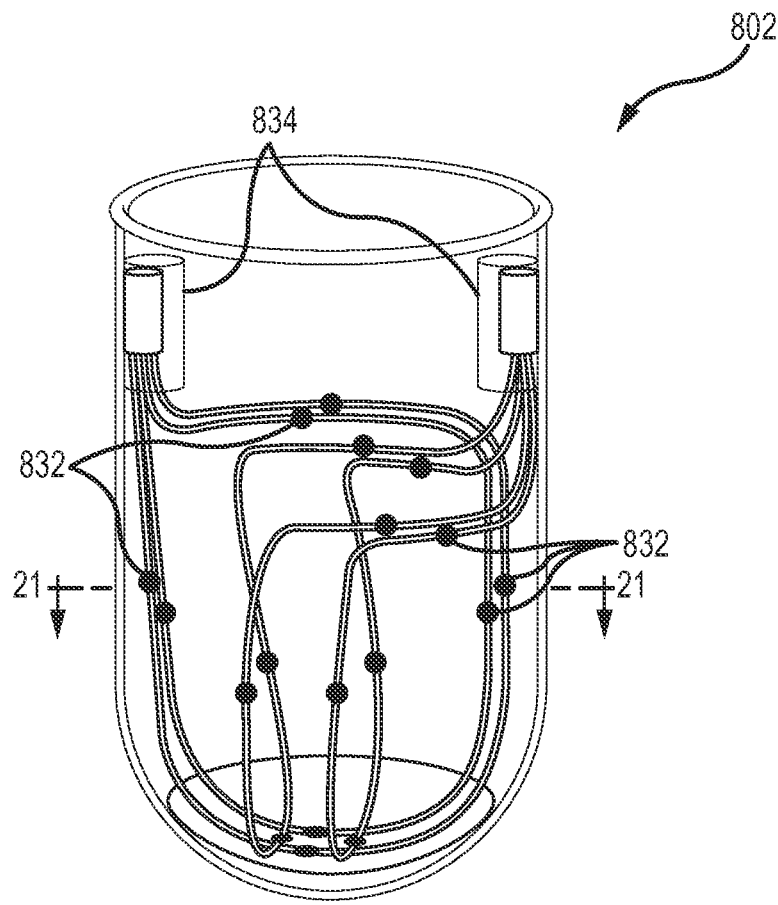
FIG. 20 illustrates a perspective view of another exemplary retrieval bag.
Figure 21:
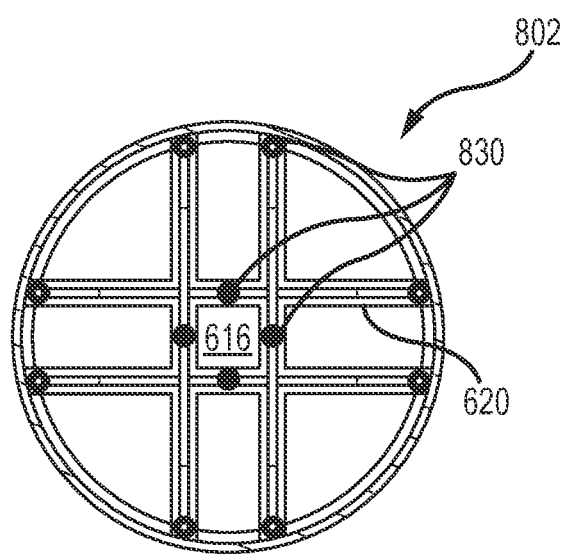
FIG. 21 illustrates a top section view of the retrieval bag of FIG. 20.

Turning now to FIGS. 20-21, the retrieval bag 802 may have a first set of temporary fasteners 830 that comprises an adhesive and/or a second set of temporary fasteners 832 that comprises an adhesive, to maintain the electrodes 604, 606, 608, 610 in a pre-collection configuration and/or a patterned configuration relative to a return 616 prior to a segmentation operation. The individual or combined adhesive effect of the second set of temporary fasteners 832 may be different than the individual or combined adhesive effect of the first set of temporary fasteners 830. A third set of fasteners 834 may be similarly temporary and/or comprise an adhesive.

In some embodiments, the container 312, 612, 1312 is shaped so as to ensure the specimen 1002 is oriented in a way that facilitates predictable cutting and contact with the return 616. In some embodiments, the bottom of the container 312, 612, 1312 may be generally flat so that the specimen 1002 can sit against the arrangement of electrodes 308. The container may also have a slightly larger mouth or entry 310, 614 to enable easier loading of the specimen. In some embodiments, the container may be long and narrow with a tapered cross-sectional area; that is, the entry may be wider than a distal or closed portion of the container. A relatively long and narrow container may be more suitable for longer specimens, such as colon, where it may be advantageous to segment along the length of the specimen. In this case a feature that generally cinches or compresses the bag may be added to hold the tissue specimen along its length.

Figure 22:
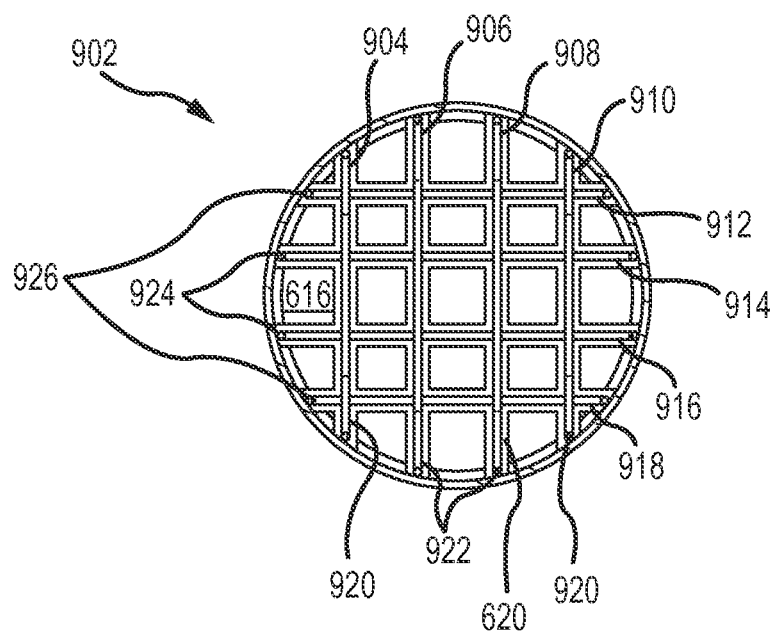
FIG. 22 illustrates a top section view of an exemplary wire configuration.
Figure 23:
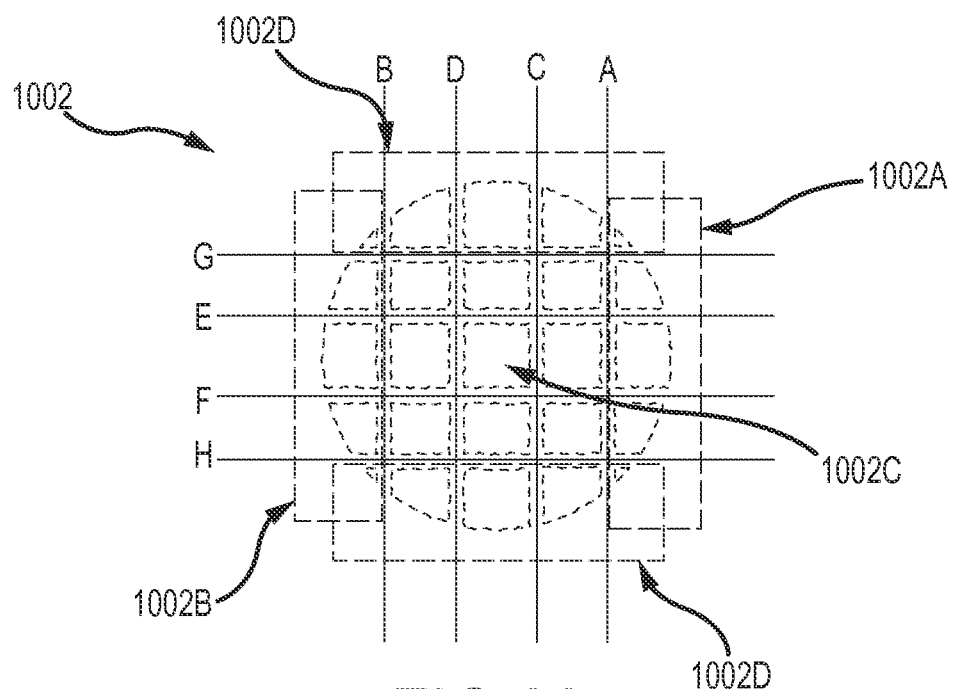
FIG. 23 illustrates a top section view of another exemplary wire configuration.

With reference now to FIGS. 22-25, it should be understood that, although four electrodes 604, 606, 608, 610 have generally been illustrated in this document, any number of electrodes may be provided so as to obtain a desired segmentation of the specimen 1002. For example, as illustrated in FIGS. 22-23, eight electrodes 904, 906, 908, 910, 912, 914, 916, 918 may be provided. In some embodiments, four electrode sets 920, 922, 924, 926 may be provided.

As illustrated in FIG. 23, in some embodiments, a first electrode set 920 may be provided and configured to segment a peripheral region or regions 1002a, 1002b from the specimen 1002 in a first plane A and/or a second plane B. A second electrode set 922 may segment a central region or regions 1002c from the specimen 1002 in third and/or fourth planes C, D. A third electrode set 924 may segment a central region 1002c from the specimen 1002 in fifth and/or sixth planes E, F, and a fourth electrode set 926 may segment a peripheral region or regions 1002d from the specimen in seventh and/or eighth planes G, H. Some of the planes A, B, C, D may be perpendicular or transverse to others of the planes E, F, G, H. In some embodiments, peripheral cuts are made prior to central cuts, while in some embodiments, central cuts are made prior to peripheral cuts. As illustrated in FIG. 23, cuts in planes A and B are made prior to cuts in planes C and D, while cuts made in planes E and F are made prior to cuts made in planes G and H. Those of skill in the art will recognize that the tissue removal device may be configured to provide an order of segmentation steps that results in the cleanest cuts possible and/or the least potential for contamination of other tissue or destruction of evidence of prior tissue disease or damage. These steps may be configured for convenience of manufacturing to ensure that the wire set closest to the tissue is activated first, allowing the next closest set to be activated next, and so on, until all of the wire sets are activated. In some embodiments, the sequence may be selected to ensure reliability of the cuts. In some embodiments, peripheral cuts are made first, while the tissue specimen in is its most rigid structural form, while central cuts follow. In some embodiments, however, a central cut may be made prior to peripheral cuts, depending on the particular application and specimen at hand.

Figure 24:
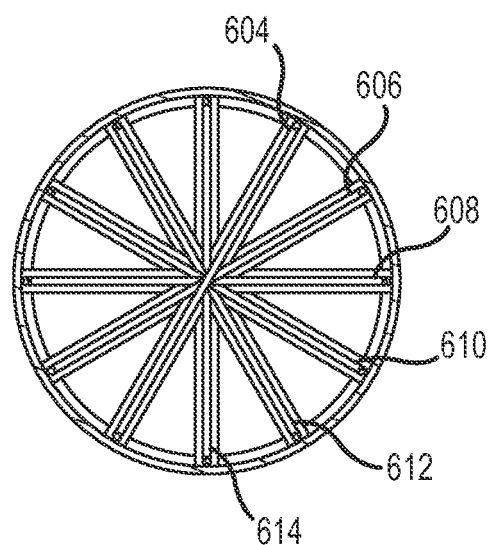
FIG. 24 illustrates a top section view of another exemplary wire configuration.
Figure 25:
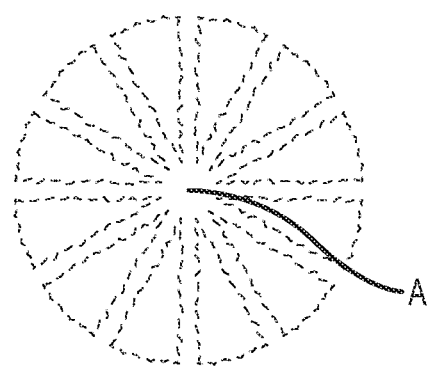
FIG. 25 illustrates a top section view of another exemplary wire configuration.

With reference now to FIGS. 24-25, it should be understood that the electrodes 604, 606, 608, 610, 612 may be arranged so as to segment the tissue 1002 in any order or shape desired; as illustrated, six electrodes 604, 606, 608, 610, 612 may be provided and positioned to result in twelve segments of the specimen. Each electrode may be positioned to segment the specimen along a plane that intersects and is pivoted about a central axis A of segmentation.

Figure 26:
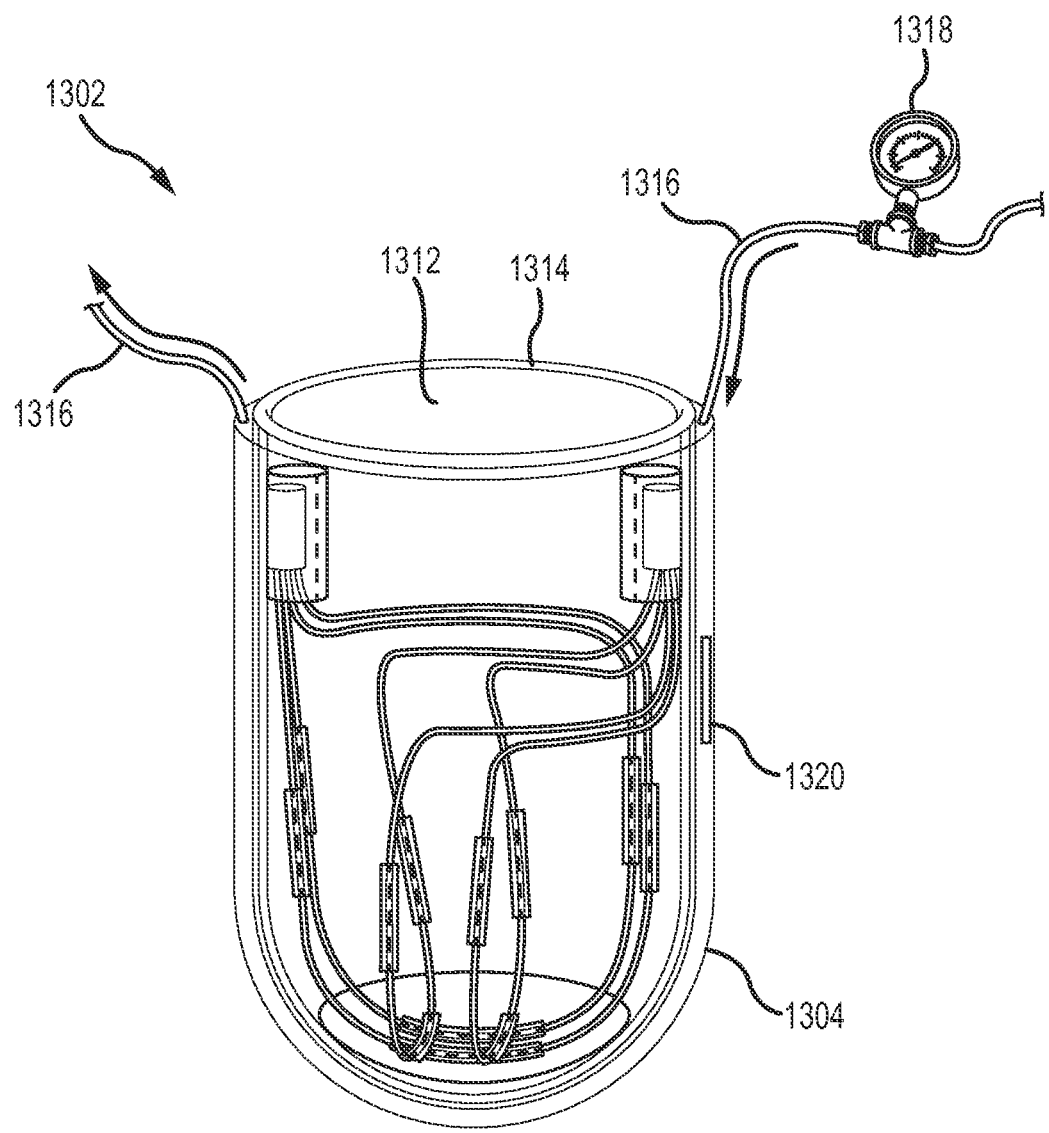
FIG. 26 illustrates a side section view of another exemplary retrieval bag.

Turning now to FIG. 26, in some embodiments, the retrieval bag 1302 may include any or all of the features previously described and illustrated in this disclosure, and, additionally, a thermally insulative layer 1304 that is coupled to or a part of a container layer 1312 having an entry 1314. The insulative layer 1304 may be made of the same or a different material than the rest of the container 1312. In some embodiments, the insulative layer 1304 includes fluid-filled and/or gas-filled pockets to insulate patient tissue or other regions of the cavity 1000 from thermal damage during the segmentation process. In some embodiments, the insulative layer 1304 may include a filling mechanism 1316 to inflate or fill the insulative layer 1304 after the retrieval bag 1302 is deployed in the cavity 1000. In some embodiments, the filling mechanism 1316 includes a circulating mechanism 1318 such as a valve or pump to circulate a gas or fluid through the insulative layer 1304 and/or to deflate the insulative layer 1304 after the segmentation process is complete. One or more sensors 1320 may be provided in the insulative layer to detect a temperature of the insulative layer 1304 and/or a pressure of the fluid or gas inside the insulative layer 1304, which may provide an indication of proper deployment and/or damage to the retrieval bag 1302.

Figure 27:
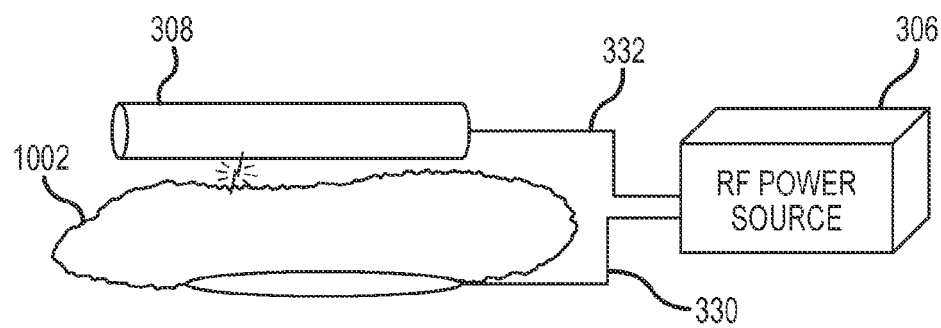
FIG. 27 illustrates a layout of an electrode and generator prior to tissue contact.
Figure 27A:
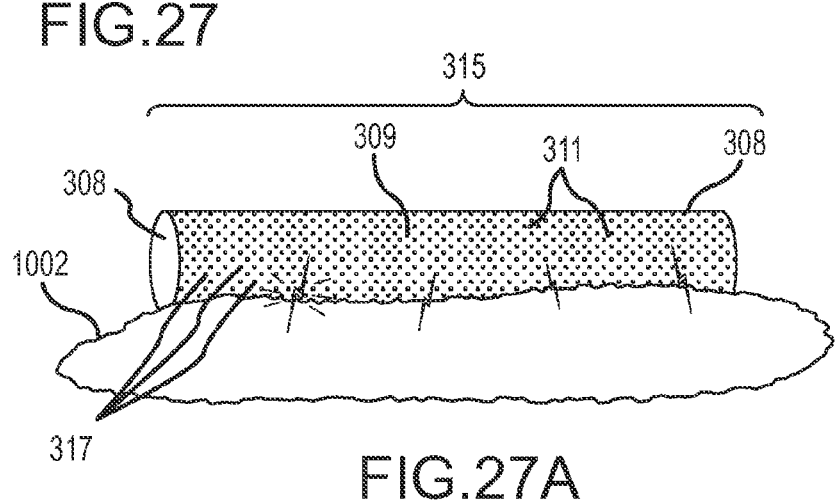
FIG. 27A illustrates an exemplary electrode in contact with tissue.
Figure 27B:
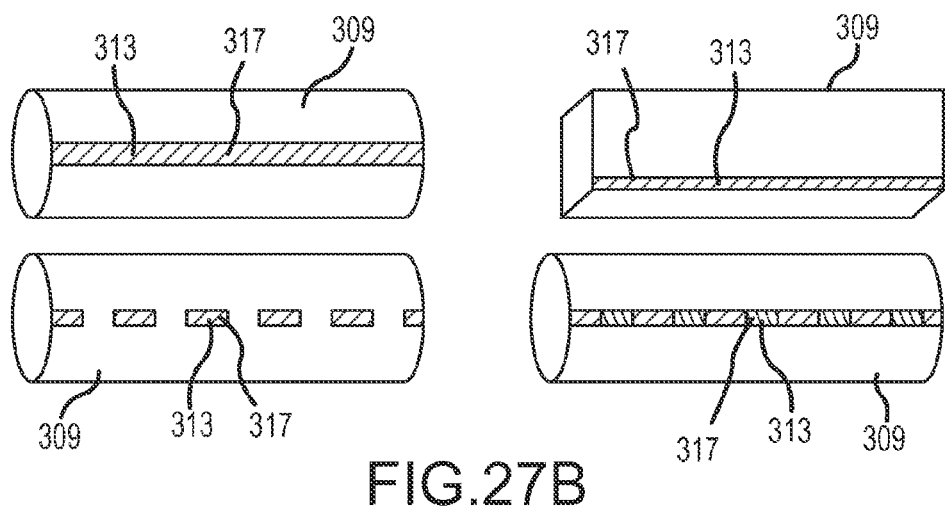
FIG. 27B illustrates several exemplary electrodes.

Turning to FIGS. 27-27B, some modes of tissue segmentation initiation are now described. As illustrated in FIG. 27, in some cases, an electrode 308 or wire 140 coupled by way of a power line 332 to a generator 306 may be placed near a tissue specimen 1002 with an air gap between the electrode 308 and the specimen 1002. The specimen 1002 may have a return 330 attached near, but not in contact with, the electrode 308. The air gap between the electrode 308 and the specimen 1002 allows an initiation of tissue segmentation through sparking or arcing when sufficient voltage is applied to the electrode 308.

Figure 28:
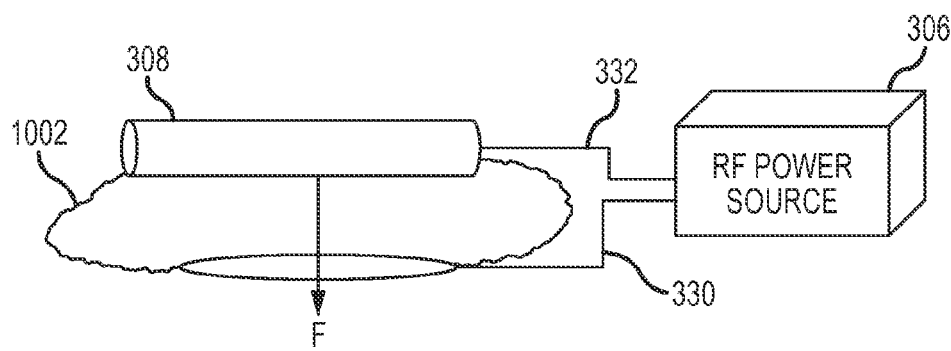
FIG. 28 illustrates an exemplary electrode in contact with tissue.
Figures 28A, 28B:
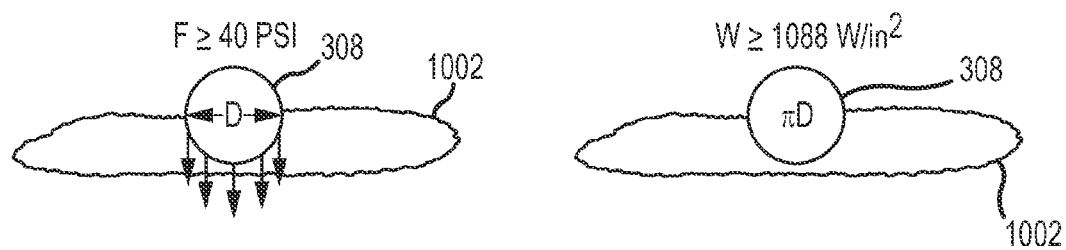
FIG. 28A illustrates estimated mechanical load characteristics of the electrode in FIG. 28.
FIG. 28B illustrates estimated electrical load characteristics of the electrode in FIG. 28.
Figure 28C:
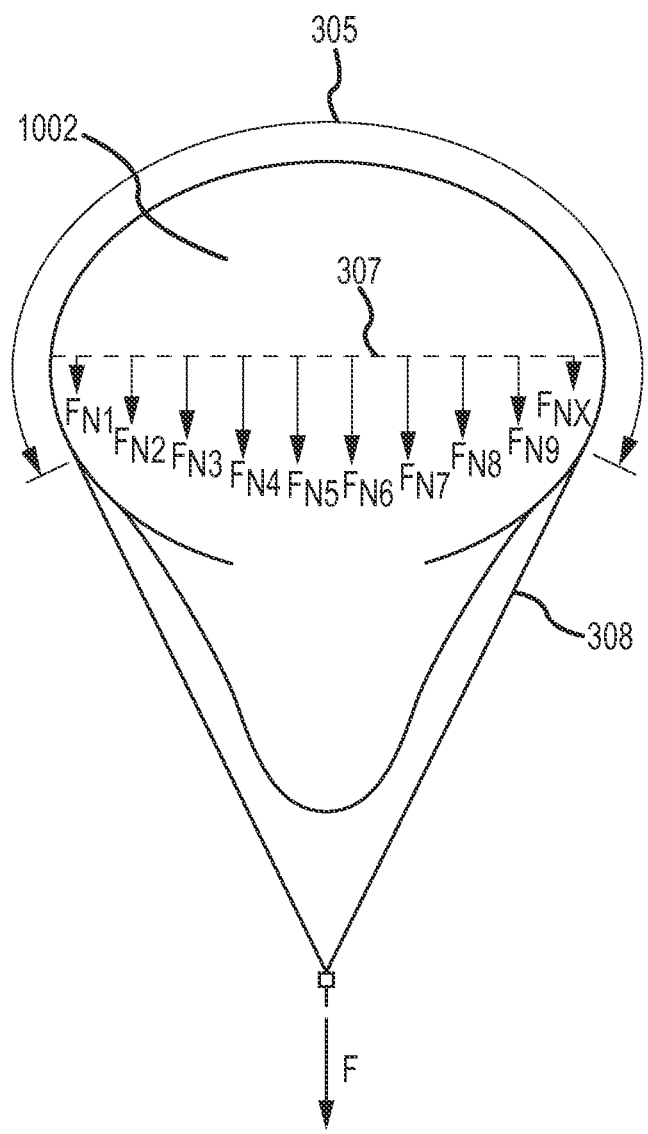
FIG. 28C illustrates estimated mechanical load characteristics of the electrode in FIG. 28.

Turning briefly to FIGS. 28C and 30, details of the active electrode are now described. The active electrode 308 may include a conductive wire 140 that may include a metallic or other materials that can carry RF current. During application of RF power, the conductive wire 140 will conduct an RF voltage applied by the generator. For the purpose of this disclosure, an exposure area 315 is the total area of the active electrode 308 that may produce an electrosurgical effect that is in contact with the tissue. Referring to the example in FIG. 28C, for an uninsulated conductive wire 140 the exposure area 315 would effectively be the same as load-bearing portion of the wire 305. Within this exposure area 315 is the active electrode surface area 317 which is the total surface area of the wire that RF current conducts between the wire and tissue. Those skilled in the art will understand that the active electrode surface area 317 may be different, and typically smaller than the exposure area 315 due to RF characteristics such as impedance variations of the wire and tissue interface. In addition, as RF cutting is in process, the active electrode surface area 317 will change due to the localized areas of arcing, movement of the wire 140 through the tissue and the subsequent exit of the wire 140 from the specimen 1002 at the completion of segmentation.

A high impedance coating 309 may be applied to the wire 308 to provide an impedance that is greater than an impedance of the bare conductive wire 140, so that the impedance observed by the RF generator will be sufficiently large enough to deliver a high voltage to the active electrode surface area 317 and across the active electrode-tissue interface. This high impedance will be dependent on many features, including but not limited to size of the wire 140, tissue properties, coating material, coating thickness, coating uniformity, and mechanical force applied by the system to the wire 140 against the tissue specimen, and may be greater than 100 ohms as observed by the generator to assist with the initiation function. Application of this coating does not affect the exposure area 315 but does affect the active electrode surface area 317, as the current will preferentially conduct to areas of lower impedance (e.g. through voids) within the exposure area 315. In some embodiments, a thinner region of the high impedance coating having a first thickness is configured to allow a current to conduct across the first thickness when a power having a preselected voltage is applied to the conductive wire.

In some embodiments, and as illustrated in FIG. 27A, when the electrode 308 is placed in direct contact with the specimen 10002, an arc sufficient to perform cutting will not be initiated unless the applied voltage is sufficiently high between the electrode 308 and specimen 1002. Because of the relationship between power, current, and voltage, an appropriate voltage level may be achieved by limiting the exposure area 315 and/or active electrode surface area 317 or tissue interface area. For example, a high impedance coating 309 having small voids 311, micro voids, and/or a thinner cross section that has a lower dielectric strength or can be dislodged, thermally dissolved or otherwise removed at lower voltages in areas may be applied to the electrode 308. The high impedance coating 309 may be configured to "degrade" under an application of power that satisfies a set of conditions, so as to increase the active electrode surface area 317, or an area of tissue contact within the exposure area 315, that is subjected to the RF power application. For the purpose of this document, the term "degrade" shall be understood to mean to reduce in dielectric strength, thickness, surface area coverage or amount, strength of adhesion, or intensity, including to wear down by erosion, to break down, to melt off, to break off, change in electrical property (such as negative temperature coefficient material), or to decompose through chemical reaction. Another means of providing an adequate voltage for initiation is to increase the localized impedance between the electrode-tissue interface, for example by delivering RF current through the tissue resulting in local desiccation, buildup of tissue proteins or eschar on the electrode surface, or with creation of an air gap or steam.

As illustrated in FIG. 27B, the active electrode surface area 317 or effective contact area for the electrical transfer may be reduced within the exposure area 315 by removing and/or thinning the coating 309 in desired patterns such as continuous or broken stripes 313 to create stripes where initiating or arcing may occur. As previously described, two mechanisms simultaneously occur to provide the cutting performance. The RF energy creates a vaporization of tissue cells near the active electrode 308 and the mechanical load F separates the tissue structures. The current provided by the RF energy performs the vaporization and is related to the current density, while the power provides the energy necessary to maintain the arcing for the duration of the cut and can be measured by the power density. For the purposes of this document, the power density will be the total power delivered by the generator divided by the exposure area 315. As the active electrode contact area is reduced, the resulting current and power density is increased resulting in an improved tissue vaporization.

With reference now to FIGS. 28-28C, once an initial arcing has occurred, the specimen 1002 may be segmented quickly and at a relatively low temperature if a sufficient mechanical load, such as proximal force F, is applied in combination with an adequate current and power density. As illustrated in FIG. 28A, in some embodiments, the tissue removal device 100, 200, 300, 400 may be configured to apply a proximal force F that results in an applied load on each electrode 140, 308 that is greater than about 275 kPa (or about 40 psi). The total load 307 applied by the electrode 308 may be generally estimated by the force F divided by the load-bearing portion 305 of the wire or the area of its projection on a plane perpendicular to the direction of the pressure. This is also called the "projected area" as defined by Lowe and Bevis, *Machine Design,* 1908, the contents of which are herein incorporated by reference. In the example illustrated, a round electrode 308, the diameter D of the electrode multiplied by the projected width of the tissue specimen 1002 in the plane of the wire cut is the load bearing or projected area.

With reference to FIG. 28B, the tissue removal device 100, 200, 300, 400 may be configured to apply a power density that is greater than about 168 Watts/cm$^2$ (or about 1088 Watts/in$^2$). The power density applied is determined or confirmed by the applied power (in Watts) and the surface area of the electrode(s) 140, 308 in contact with the specimen 1002. In the case of a round electrode 308, the power density is pi multiplied by the diameter of the electrode and the length of the electrode in contact with the specimen (or $\pi DL$).

As can be understood from consideration of FIGS. 28A-28B, the length of the electrode 140, 308 in contact with the specimen 1002 is not necessarily the same as the length of the electrode 308 that applies a force on the tissue that is normal to the direction of cut; however, this difference may be negligible in some cases, depending on the shape of the specimen 1002 and the design of the electrode 308.

In some embodiments, as the specimen 1002 is segmented and resulting in less contact between the specimen 1002 and the electrode(s) 308, the tissue removal device 100, 200, 300, 400 may be configured to reduce the proximal force F applied and/or the power levels to maintain an efficient cut that is clean and without excessive heating. In some embodiments, the first and/or second springs 512, 514 may be configured to apply a reduced proximal force F as the actuator 504 approaches a fully retracted state so as to reduce the proximal force F as the specimen 1002 nears a fully segmented state. In some embodiments, a feedback system may be provided wherein the generator 306 is responsive to a determination that the specimen 1002 is nearing a fully segmented state. In some embodiments, the power may be adjusted as the cut is being performed. As the wire begins to exit the specimen near the completion of the cut, the tissue surface area in contact with the exposure begins to reduce due to the geometry of the specimen and the loop electrode 140, 308. This reduction in area increases the mechanical load per area, as well as the power density. This effect will provide an increased power density if the settings are maintained and can have an acceleration effect at the completion of the cut with a constant force load applied. Adjusting the power delivered to the wire or wire set can compensate for this effect, providing a more consistent cut at the completion. In some embodiments, tissue impedance trends are monitored by a sensor that identifies the location of the pull assembly as it advances within the lumen.

Figure 29:
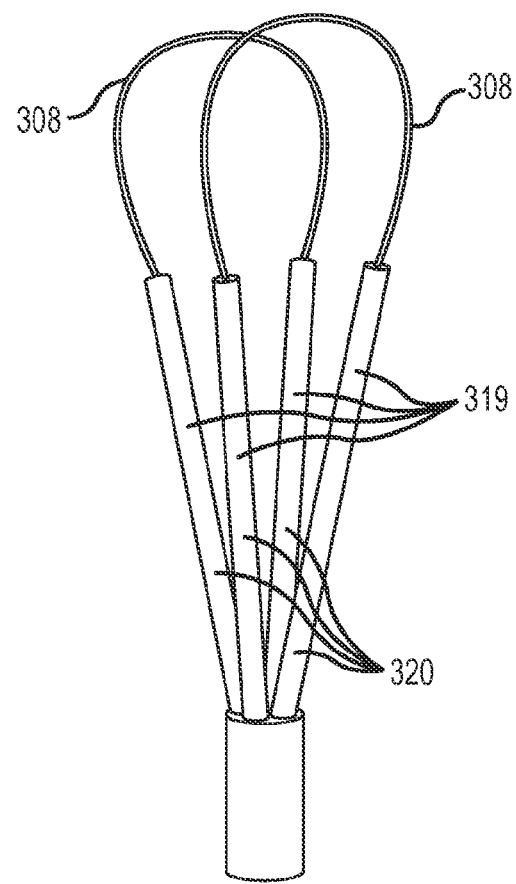
FIG. 29 illustrates a side view of another wire configuration.
Figure 30:
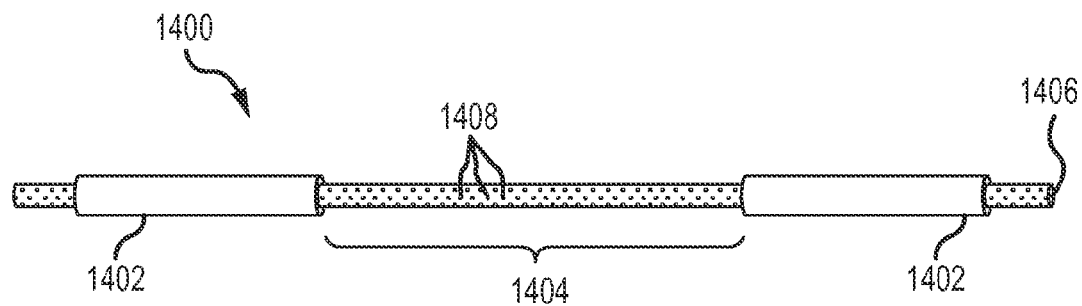
FIG. 30 illustrates a side view of another wire configuration.
Figure 31A:
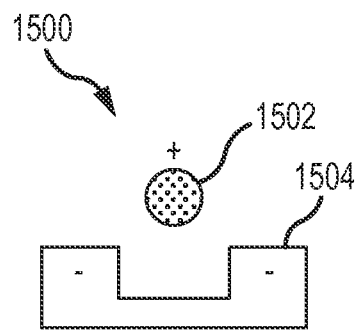
FIG. 31A illustrates a dissector and end effector using an exemplary wire configuration.
Figure 31B:
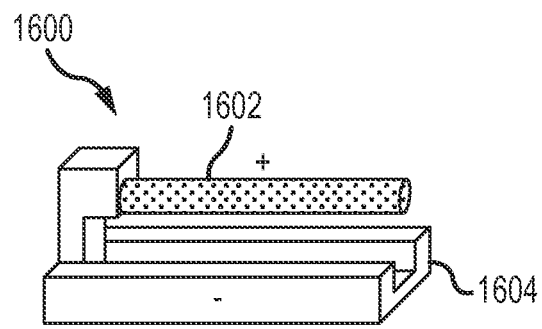
FIG. 31B illustrates an exemplary dissecting tip using an exemplary wire configuration.
Figure 31C:
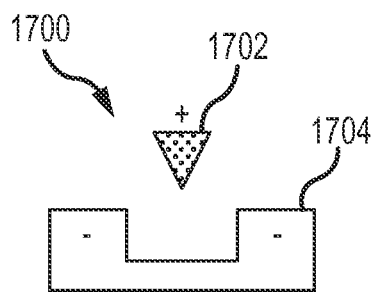
FIG. 31C illustrates another exemplary wire configuration with an opposing jaw.
Figure 31D:
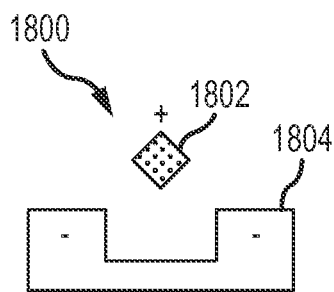
FIG. 31D illustrates another exemplary wire configuration with an opposing jaw.
Figure 31E:
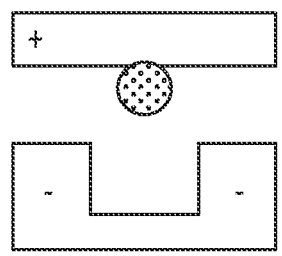
FIG. 31E illustrates another exemplary wire configuration with an opposing jaw.
Figure 31F:
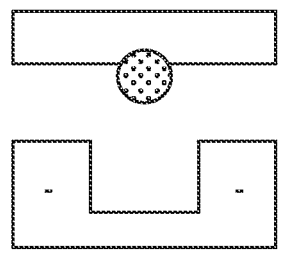
FIG. 31F illustrates another exemplary wire configuration with an opposing jaw.

Turning now to FIG. 29, another configuration of the electrode(s) 308 is described. As illustrated, the proximal portions 320 of the electrode(s) 308 may include an inactive electrosurgical area, which may be an insulative portion 319. The inactive electrosurgical area may include a thicker coating 309, an impedance that is greater than an impedance of an exposure area and/or active electrode surface area, a bond to the conductive wire that is stronger than a bond of the exposure area to the conductive wire, and/or other insulating material including semi-rigid tubing. This portion 319 is intended to be an insulator that will not conduct current and will not be part of the exposure area 315 or active electrode surface area 317. This will minimize the exposure area 315, or the surface area of the electrode(s) 308 that is in contact with the specimen 1002. The portion 319 may also provide a physical support to the electrode(s) 308 to reduce the chance of electrode breakage during segmentation, deployment, etc.

Segment size repeatability may be necessary to ensure that the user can easily remove the segments from the retrieval bag 302. Several approaches may be incorporated to improve repeatability of the segment sizes. As disclosed previously, the positions of the wires 140, 308 relative to each other is important. The temporary holding of the wires 140, 308 to the container 312, potential joining of the wires 140, 308 together, and pretension of the wires 140, 308 prior to cutting all contribute to repeatability. In some embodiments, low temperature material loops, adhesives, or plastic bands may hold the wires 140, 308 in a position relative to the container 312, and not release until the wire 140, 308 is pulled partially through the specimen 1002. In some embodiments, a shape memory alloy may be used to keep the electrodes 308 in a particular position before or during cutting. For example, the shape memory alloy may be attached to the distal portion of the electrode wires 140, 308 in combination with an insulative sleeve. Some embodiments may include rigid, hinged or non-hinged members that connect the cutting wires 140 to the connector rods 516, 518 or actuator. These rigid members could be utilized to maintain the wire electrodes 140, 308 in a specific orientation, or spacing, during the cut. In addition, for instruments that utilize more than one set of electrodes 422, 424 pulled serially, the order and position of the electrodes 422, 424 may impact repeatability. For example, it may be advantageous to have the electrode sets 422, 424 be positioned symmetrically about the specimen 1002, rather than pulling on one side of the specimen 1002 only, such that the specimen 1002 may rotate within the container 312.

In some embodiments, the specimen 1002 may be secured using various features of the bag 302 prior to and during segmentation, so as to improve the repeatability of the resulting segments or the cuts themselves. For example, some embodiments include inflatable bladders that compress specific locations of the specimen 1002. The inflatable bladders may be placed inside the spacing of the wires 140 in the bag 302 so that the wires 140 are not constricted by this compression and are allowed to freely detach from the bag 302 and make contact with the tissue specimen 1002. Compressing the specimen 1002 before and during segmentation allows the specimen 1002 to maintain the overall shape during the segmentation process. In some embodiments, inflation of the inflatable bladders is staged so that, during loading of the tissue specimen 1002, the entry 310 of the bag and a subset of features along the axis of the bag are inflated to provide some form and rigidity to the bag to assist in capturing the tissue specimen. The bag can then be deflated to allow exteriorization. The bag 302 can then be re-inflated either to the same level previously described or to a higher pressure, or at different portions of the bag 302 to assist in securing the tissue specimen in the intended orientation, or with the addition of inflated features at each location between wires. This provides the mechanical support not only of the tissue specimen during cutting but can also provide retraction to hold the specimen with reference to the incision site.

FIG. 30 illustrates a more detailed view of the electrode 1400 used in some embodiments. As illustrated, the electrode(s) 1400 may have an exposure area 315, 1404 that contains an active electrode surface area 317, 1408 and one or more areas having an insulative portion 1402 that may be achieved by a thicker coating or with other insulating material including a semi-rigid tubing and/or heat shrink. For the purpose of this document, the exposure area 1404 is considered any area where the high impedance coating is removed from a central conductive wire, is thin, or has voids therein, thereby reducing the impedance in a generalized area. Within this exposure area 315, 1404 is the active electrode surface area 317, 1408 which is the total surface area of the wire that RF current conducts between the wire and tissue. In FIG. 30, the active electrode surface area 1408 is the sum total of the voids across which RF current is conducted. As previously described, the active electrode surface area 317, 1408 will change due to the localized areas of arcing, movement of the wire 140 through the tissue and the subsequent exit of the electrode 1400 from the tissue specimen 1002 at the completion of segmentation.

Turning now to FIGS. 31A-31F, aspects of an application of the electrodes outside of tissue or specimen segmentation is now described. Use of RF wires for cutting has other known applications in surgery such as TURP (prostatectomy) electrodes and polypectomy snares. These applications use much shorter wires than are necessarily needed for removing large specimens. However, a coated wire with a controlled mechanical load and minimum power density could benefit those instruments as well by creating a more optimized tissue effect that requires less "art" by the surgeon or user. In some embodiments, it may be beneficial to further optimize or lower the mechanical load or power densities even further to create a coagulation effect rather than a low thermal cutting effect. This may be facilitated by sensors that sense the tissue and adjust the power and/or mechanical force to provide the proper amount of coagulation with reduced thermal spread or by the waveform and algorithm of power and mechanical load delivery. The return electrode may be the patient return pad or may be an electrode placed on or near wire cutting instrument.

In currently-available devices, recommended power levels may be provided by the manufacturers; however, these devices still require the user to determine the appropriate amount of tension or mechanical load to apply to the tissue. In devices herein disclosed, Applicants provide a means for overcoming the inherent variability in user-controlled mechanical loading by providing, in some embodiments, a controlled mechanical load or power. The controlled mechanical load or power in these instruments may provide lower thermal spread while ensuring adequate coagulation or stopping blood flow in polypectomies, and result easier to use instruments. This power control may be incorporate "Cut" and "Coag" waveforms on standard electrosurgical generators used today or may be unique waveforms or control algorithms.

Another potential application for the disclosed wire cutting technology may be for surgical dissectors in tissues such as colectomies or Lap Nissan procedures, as illustrated in FIG. 31A-31F. Ultrasonic dissectors are already commonly used to serve this function, but have several disadvantages including, but not limited to, instrument and generator costs. In some embodiments, the higher impedance coated wires 140, 308 may be part of a radiofrequency dissector to allow for initiation of a cut at lower power levels and more rapidly than a bare wire or bare jaw, enabling potentially longer dissection jaw lengths, faster dissection times, and potentially lower costs compared to traditional ultrasonic dissectors. The instrument 1500, 1600, 1700, 1800, 1900, 2000 may plug into commonly available electrosurgical generators. In addition, the mechanical load may be controlled for the user to ensure optimized cutting and coagulation times. In some embodiments, and as illustrated in FIGS. 31A-31F with varying cross sectional shapes, the coated wire 1502, 1602, 1702, 1802 may compose one half of a dissector end effector while the other half of the end effector or opposing jaw 1504, 1604, 1704, 1804 is composed of the "return" or second electrode of the bipolar instrument. The wire or first electrode 1502, 1602, 1702, 1802 may fit within an opposing slot in the return or second electrode to allow it to pass completely through the tissue during dissection. The instrument 1500, 1600, 1700, 1800, 1900, 2000 may be designed such that the first electrode 1502, 1602, 1702, 1802 cannot contact the slot surface either through use of a stop that mechanically does not allow first electrode to extend to the slot surface, or with an electrical insulator on the slot surface at the location of contact. Power density (or current density) and mechanical loads may be optimized and vary to create a user selected cutting mode versus coagulation mode. Alternatively, mechanical loads may be controlled to be the same, regardless of mode, while a different radio frequency waveform may be utilized to create optimized cut and coagulation tissue effects. "Cut" and "Coag" waveforms on standard electrosurgical generators used today may be used to create the optimized cut and coagulation tissue effects. In some embodiments, unique waveforms or control algorithms to the dissecting instrument 1500, 1600, 1700, 1800, 1900, 2000 may create the optimized cut and coagulation tissue effects.

As described herein, a means to improve the natural limit of a generator output into a low impedance is to create a generator output that can provide a higher voltage during the cut initiation function, and an output that can provide a higher current during the cut sustaining function. One embodiment is with a generator designed for optimized performance at the impedance range typically observed in tissue segmentation with a wire. As standard electrosurgical generators are designed for maximum power transfer around 300 to 500 ohms, operation in the 70 to 300 ohm range results in either reduced power output at the lower end of this range or reduced current at the higher end of this range. An ideal generator for tissue specimen segmentation would have a maximum power transfer at a range that includes less than 300 ohms and an increased current limit of greater than 1.2 amps. A generator with this type of output would be able to drive a larger exposure, or more wires with the same exposure, would have the voltage necessary to create an initiation with a lower impedance coating and would have more current available for cutting during the sustaining function compared to existing generators. Additionally, different RF amplifier topologies may be used that provide similar benefits for lower impedance operation. One example is Dual Current-Mode Controller as presented by Daniel A. Friedrichs, Robert W. Erickson and James Gilbert presented in the IEEE TRANSACTIONS ON BIOMEDICAL CIRCUITS AND SYSTEMS, VOL. 6, NO. 1, FEBRUARY 2012, the contents of which are incorporated herein by reference. This topology does not use the resonant output to create a sinewave and therefore does not have the same natural limitations of typical amplifiers at lower and higher impedance loads. This topology also has the ability to change the power output very quickly so that it can be biased for higher voltage during initiation and transitioned to higher current as the initiation event occurs.

As previously mentioned, the device or system may include features to ensure proper operation and reduce the likelihood of inadvertent RF thermal damage. These features may require additional control and monitoring circuits that may not be available in existing electrosurgical generators. The system may either incorporate these into the actuator 304 or with a specialized RF generator designed for optimized performance, usability and monitoring of parameters to reduce the likelihood of inadvertent RF thermal damage. Alternatively it may be advantageous to incorporate these features into a separate controller that would be used in conjunction with existing electrosurgical generators. The controller will be coupled to the generator 306, such that the RF output power and return connections (monopolar or bipolar) will be provided to the controller. The controller might communicate instructions to the user via textual displays, graphical displays, numerical displays, visual indicators, audio indicators or by other means to instruct the user on how to set-up and operate the system during use. The controller will also be coupled to the active electrodes 308 and return electrode 330 so that RF output power will be provided if all predefined conditions are satisfied as determined by control logic within the controller. This control logic will be performed by electrical circuits and a control method such as a microprocessor, FPGA, analog control circuit, or other similar control device. Additionally, the controller will be coupled to the actuator 304 to receive sensor outputs with monitoring or status information and to provide control for proper operation of the device. In addition, electrical and mechanical sensors and control circuitry may be incorporated in any combination of an RF generator, controller, actuator, or another accessory that may be used in conjunction with the system either directly connected or with wireless communication.

The sensors or control circuits may be used to provide information such as, but not limited to, force sensors coupled to the actuator to provide the force applied to the wires by the pull mechanism prior and after pre-tension and during and after cutting, force sensors coupled to the containment assembly to provide the force applied to the containment assembly during pre-tension and cutting, pressure sensors within the containment assembly to provide the compression force applied by the containment assembly to the tissue specimen, translation sensors or location indicators to provide the rate of travel or confirm the advancement of the pull mechanism during cutting or a cutting complete indication, current and voltage sensors to provide the RF current and voltage delivered to the actuator during cutting, temperature sensors, such as thermistors, a current and voltage sensor that monitors an interrogation signal either between the wire sets and return electrode or different parts of the return electrode to monitor the contact quality of the tissue specimen with the return electrode, thermocouples or other temperature sensitive semi-conductors, within the actuator or containment assembly to provide the localized temperature of specific locations. Pressure or flow sensors coupled to inflatable features within the containment assembly provide pressure or inflation information of any air or fluid used within the system. The control circuits may also provide control from the controller to the actuator such as, but not limited to, enable and/or disable of RF power to the actuator or wire set, selection of the specific pull mechanism for cutting, RF activation requests from the actuator and to the RF generator, adjust or limit the RF power delivered to the actuator with amplitude modulation, pulse modulation, or by requesting a change in the power setting to the RF generator, and inflation or deflation of any containment assembly features.

It is understood by those skilled in the art that with a combination of sensor outputs and control methods described above, the controller or RF generator may provide closed loop control of the RF output around mechanical cutting speed or translation, temperature of the tissue or other of points in the system, by the current or impedance of the tissue. In addition, the sensors and control methods allow monitoring of unintended conditions such as a short of the wire sets and return, a stop in the advancement of the actuator pull mechanism, adequate contact of the tissue specimen with the return electrode, or other conditions that can be quickly addressed by the controller.

Figure 32:
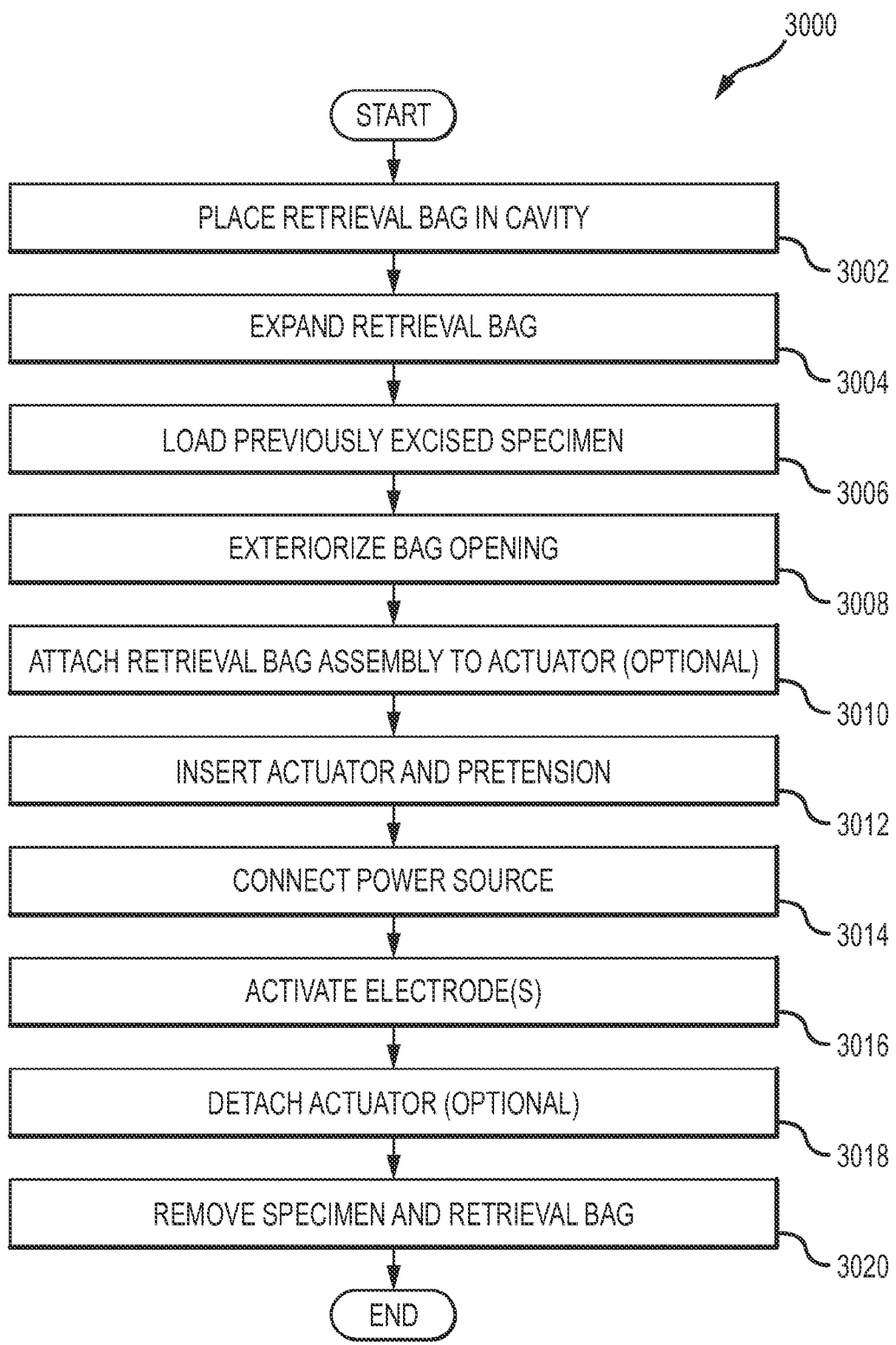
FIG. 32 illustrates an exemplary method of removing tissue from a patient.

Turning now to FIG. 32, a method 3000 of removing a large tissue specimen is now described. For the purpose of this document, a large tissue specimen is one that is larger in size than the incision or entry used to perform the excision or surgery. For example a 20 mm diameter specimen may be considered large if a 3 to 5 mm incision were used to extract the specimen.

The method 3000 includes placing 3002 a retrieval bag into a cavity of a patient, such as through a trocar, a natural body opening, and/or incision in the patient. In some embodiments, the retrieval bag may be placed in the cavity using a deployment instrument 1004 and/or cannula as illustrated in FIG. 1. In some embodiments, the retrieval bag may be placed in the cavity using an actuator as illustrated in FIG. 6. The retrieval bag may be any retrieval bag described with reference to any one of the previous figures in this document.

The method 3000 also includes expanding 3004 the retrieval bag. Expanding 3004 may be achieved by, for example, removing a restricting cannula and allowing a biasing mechanism such as a memory-retaining material near an opening of the bag to open, and/or expanding 3004 may include causing a deployment instrument to manipulate the bag. In some embodiments, expanding 3004 may include allowing a biasing force in a wall of the bag, such as biasing wires or electrodes 408 to cause the retrieval bag to open.

The method 3000 also includes loading 3006 a previously excised specimen. Loading 3006 may be achieved by manipulating the specimen towards and through an entry in the retrieval bag, as illustrated in FIGS. 1-8 of this document.

The method 3000 also includes exteriorizing 3008 an opening or entry of the retrieval bag. Exteriorizing 3008 may be achieved using, for example, a grasper 1006 to pull proximal portions of the retrieval bag towards and through the patient opening, as illustrated in FIGS. 3-5 using a bag feature that may include a tab near the bag opening, a drawstring, the return cable, a proximal end of an electrode or electrode set, or other feature integrated into the bag for exteriorization, or exteriorizing 3008 may be achieved using, for example, the tissue removal device 400 as illustrated in FIGS. 6-8. Exteriorizing 3008 may be assisted by using a pull device in the actuator 404 and/or by applying a proximal force F on one or more of the electrodes 408.

In some embodiments, the method 3000 includes attaching the retrieval bag assembly to an actuator, and may be achieved using the tissue removal device 300 illustrated in FIGS. 3-6 and/or the actuator illustrated in FIGS. 9-13. Attaching the retrieval bag assembly to an actuator may include crimping one or more sets of electrodes, and inserting the proximal portions of the electrodes into respective distal portions or respective slots in one or more connector rods of respective pull assemblies, as illustrated in FIGS. 9-13.

The method 3000 also includes pre-tensioning 3012 the electrode(s). Pre-tensioning 3012 may include inserting a distal portion of the actuator into the patient body and causing the actuator to apply a proximal force F onto the electrode(s). The specimen may be drawn towards an interior wall of the cavity and/or the actuator may be drawn towards the specimen. In some embodiments, the pre-tensioning force may differ from the applied load during cutting.

The method 3000 also includes connecting a power source 3014. Connecting a power source may include connecting a return electrode and/or a power cable to the actuator as illustrated in FIGS. 3-13.

The method 3000 also includes activating the electrode(s) 3016 to cause tissue segmentation. Activating the electrode(s) may include causing the generator to apply a power resulting in a power density that is greater than about 168 Watts/cm2 (or about 1088 Watts/in2), as illustrated in FIGS. 27-28C.

Constant force application for segmentation may be achieved using springs, such as linear springs, for the segmentation instrument. This controlling of force during activation may also be achieved using a number of alternative mechanisms including, but not limited to, linear actuators, composite spring assemblies, motor/gearing wind-up mechanisms. Any of these may be used to deliver a constant (or near-constant) force F which promote low-temperature segmentation without exceeding the tensile force of the cutting electrodes.

The method 3000 may include detaching 3018 the actuator, and may include detaching the actuator from the generator as illustrated in FIGS. 10-13, such as detaching the return cable that connects the actuator to the bag.

The method 3000 also includes removing 3020 the tissue specimen and the retrieval bag. The tissue specimen, after being segmented, is removable through the exteriorized retrieval bag entry. After the specimen is removed, the retrieval bag may be removed through the same opening. Those skilled in the art will readily understand that the tissue reduction and removal system can be embodied as a single use device. It may also be easily embodied with some single use components, such as the containment assembly or retrieval bag, and reusable components, such as the actuator 304 and grasper 1006. This approach has the advantage of providing a less expensive specimen removal system. It could also be embodied with a durable bag structure with single use wires and/or return electrode attached prior to the procedure.

In accordance with additional aspects, a method may include one or more of the following:

Aspect 1:

A method of extracting a tissue specimen from a patient, wherein the specimen has a cross section that is larger than a cross section of a passage through which the specimen is to be extracted, the method comprising: introducing a tissue removal system into a cavity of the patient, the tissue removal system having a retrieval bag and a plurality of electrodes, at least one of the plurality of electrodes having a high impedance coating configured to allow an electrosurgical current to flow when a set of conditions are satisfied; deploying the system in the patient; loading a previously excised specimen into the retrieval bag; exteriorizing an opening of the retrieval bag; applying an electrosurgical power that satisfies the set of conditions to the at least one of the plurality of electrodes to cause current to flow across an active electrode surface area of the at least one of the plurality of electrodes; segmenting the specimen by applying the electrosurgical power to a surface area of the specimen in contact with the active electrode surface area of the at least one of the plurality of electrodes and applying a mechanical force to a surface area of the specimen in contact with the at least one of the plurality of electrodes; and extracting the segmented specimen through the exteriorized opening of the retrieval bag.

Aspect 2:

The method of aspect 1, further comprising: detaching the at least one of the plurality of electrodes from the flexible container.

Aspect 3:

The method of aspect 1, further comprising at least one of: causing an arc to initiate through at least one of a micro void, a lower impedance region, a thin region, or a weak-bond region of the high impedance coating; or applying an electrosurgical power to the high impedance coating and causing a portion of the high impedance coating to degrade.

Aspect 4:

The method of aspect 1, further comprising: applying an electrosurgical power to the specimen through the active electrode surface area, the active electrode surface area defined by a thin region, a void, or a degraded region in the high impedance coating; and insulating the specimen from the electrosurgical power at a thick region of the high impedance coating.

Aspect 5:

The method of aspect 1, further comprising: applying an electrosurgical power having a power density of at least 168 Watts per square centimeter of the specimen in contact with the exposure area; and applying a pressure of at least 275 kPa on an area of the specimen in contact with a load-bearing portion of the at least one of the plurality of electrodes.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A tissue removal system for extracting a tissue specimen from a patient, the system comprising:
    a retrieval bag having a flexible container with an opening;
    a first electrode coupled to an interior of the flexible container, the first electrode having a conductive wire with an exposure area, a first load-bearing area, a coating having a first active electrode surface area and configured to provide an impedance between the tissue specimen and the first electrode, wherein the first active electrode surface area is less than the exposure area; and
    a return electrode; wherein
    the coating is configured to degrade during application of electrosurgical power and wherein the degradation expands the first active electrode surface area during the application of the electrosurgical power.

2. The tissue removal system of claim 1, wherein:
    the coating is configured to degrade when the generator applies a voltage sufficient to allow an arc to initiate across the coating.

3. The tissue removal system of claim 2, wherein:
    the coating has a first thickness and a second thickness greater than the first thickness; and
    the first thickness of the coating is configured to allow a current to conduct across the first thickness when the electrosurgical power having a preselected power density is applied to the conductive wire.

4. The tissue removal system of claim 1, wherein:
    the exposure area is defined by a region of the coating that has a plurality of micro voids, has a reduced impedance, has a reduced thickness, exposes the conductive wire, or any combination thereof.

5. The tissue removal system of claim 1, wherein:
    the first active electrode surface area is defined by a total surface area of the first electrode that is configured to conduct RF current between the conductive wire and the specimen.

6. The tissue removal system of claim 1, wherein:
    the coating is configured to degrade when at least a portion of the coating is raised to a temperature of 160 degrees Celsius.

7. The tissue removal system of claim 1, wherein:
    the tissue removal system comprises a second electrode coupled to the interior of the container; and an actuator, the actuator configured to apply a first pull force on the first electrode prior to applying a second pull force on the second electrode; and
    the first pull force is selected to apply a pressure of 275 kPa or more at the first load-bearing area.

8. The tissue removal system of claim 1, wherein:
    the electrosurgical power is at least 168 Watts per square centimeter of the exposure area.

9. The tissue removal system of claim 1, further comprising:
    a second electrode removably coupled to the interior of the flexible container, the second electrode having a conductive wire with an exposure area, a second load-bearing area, and a coating having a second active electrode surface area and configured to provide an impedance between the tissue specimen and the second electrode, wherein the second active electrode surface area is less than the second exposure area; wherein
    the coating of the second electrode is configured to degrade during application of electrosurgical power to the second electrode and wherein the degradation of the second electrode expands the second active electrode surface area during the application of the electrosurgical power to the second electrode;

a generator coupled to the first electrode and the second electrode, the generator configured to cause the electrosurgical power to the first electrode to commence prior to causing the electrosurgical power to the second electrode to commence; and an actuator configured to apply a first pull force on the first electrode prior to applying a second pull force on the second electrode.

10. The tissue removal system of claim 1, further comprising:

a second electrode coupled to the interior of the flexible container; and wherein:

each of the first electrode and the second electrode is spring-biased away from the other one of the first electrode and the second electrode.

11. The tissue removal system of claim 1, wherein:

at least one temporary fastener removably couples the first electrode to the flexible container.

12. The tissue removal system of claim 1, further comprising:

a first fastener shaped and positioned to removably couple the first electrode to the flexible container and prevent the first electrode from contacting the return electrode;

a second fastener shaped and positioned to removably couple the first electrode to the flexible container in a configuration to provide a specimen receiving space; and a third fastener shaped and positioned to couple a proximal portion of the first electrode to the flexible container.

13. The tissue removal system of claim 12, wherein:

the proximal portion of the first electrode is removably coupled to a first pull assembly, the first pull assembly configured to selectively apply a mechanical pull force on the first electrode.

14. The tissue removal system of claim 1, further comprising:

a first electrode set having a plurality of electrodes removably coupled to an interior of the flexible container, each of the plurality of electrodes having a first load-bearing area, the first electrode set further having the first electrode;

a second electrode set having a plurality of electrodes removably coupled to the interior of the flexible container;

an actuator having a first pull assembly coupled to a proximal portion of the first electrode set and configured to apply a first pull force on the first electrode set, a second pull assembly coupled to a proximal portion of the second electrode set and configured to apply a second pull force on the second electrode set; and a generator coupled to the first and second electrode sets, the generator configured to provide a first electrosurgical power to the first electrode set and a second electrosurgical power to the second electrode set.

15. The tissue removal system of claim 1, wherein:

the tissue removal system comprises a lumen having an interior passage; and the tissue removal system is configured to cut a tissue specimen into a plurality of tissue segments, each tissue segment sized to pass through the interior passage.

16. A tissue removal system for extracting a tissue specimen from a patient, the system comprising:

a tissue retrieval bag having a flexible container with an opening;

a first electrode set configured to segment the tissue specimen into a first set of a plurality of tissue segments, the first electrode set having a plurality of electrodes removably coupled to an interior of the flexible container, each of the plurality of electrodes having a conductive wire with a load-bearing area, at least one of the plurality of electrodes having a high impedance coating, an exposure area, and a first active electrode surface area, the first active electrode surface area less than the exposure area;

a second electrode set configured to segment the first set of the plurality of tissue segments into a second set of a plurality of tissue segments, the second electrode set having a plurality of electrodes removably coupled to the interior of the flexible container;

an actuator having a first pull assembly coupled to a proximal portion of the first electrode set and configured to apply a first pull force on the first electrode set, the first pull force configured to cause the tissue specimen to segment into the first set of the plurality of tissue segments, a second pull assembly coupled to a proximal portion of the second electrode set and configured to apply a second pull force on the second electrode set, the second pull force configured to cause the first set of plurality of tissue segments into the second set of the plurality of tissue segments; and a return electrode; wherein the actuator is configured to commence applying the first pull force prior to commencing applying the second pull force; and wherein the high impedance coating of the at least one of the plurality of electrodes in the first electrode set is configured to degrade during application of electrosurgical power to expand the first active electrode surface area.

17. The tissue removal system of claim 16, wherein:

the high impedance coating of the at least one of the plurality of electrodes in the first electrode set is configured to degrade when a voltage sufficient to allow an arc across the high impedance coating is applied.

18. The tissue removal system of claim 17, wherein:

the high impedance coating has a first thickness and a second thickness greater than the first thickness;

and the first thickness of the high impedance coating is configured to allow a current to conduct across the first thickness when a power having a preselected voltage is applied to the conductive wire.

19. The tissue removal system of claim 17, wherein:

the high impedance coating of the at least one of the plurality of electrodes in the first electrode set has a first inactive electrosurgical area, the first inactive electrosurgical area having at least one of: an impedance that is greater than an impedance of the first active electrode surface area, or a bond to the conductive wire that is stronger than a bond of the exposure area to the conductive wire;

and the first active electrode surface area of the high impedance coating of the at least one of the plurality of electrodes is configured to conduct current.

20. The tissue removal system of claim 16, wherein:

the first pull force is selected to apply a pressure of 275 kPa or more; and the tissue removal system comprises a generator configured to apply an electrosurgical power density to the first electrode set, the electrosurgical power density at least 168 Watts per square centimeter of the exposure area.

21. The tissue removal system of claim 16, wherein:
the at least one of the plurality of electrodes in the first electrode set is removably coupled to the flexible container.

22. The tissue removal system of claim 16, wherein:
the proximal portion of the first electrode set is removably coupled to the first pull assembly.

23. The tissue removal system of claim 16, wherein:
the tissue removal system comprises a lumen having an interior passage; and
each of the plurality of tissue segments in the second set of the plurality of tissue segments is sized to pass through the interior passage.

24. The tissue removal system of claim 16, further comprising:
a generator coupled to the first electrode set and the second electrode set, the generator configured to apply a first electrosurgical power to the first electrode set and a second electrosurgical power to the second electrode set.

25. A tissue removal system for extracting a tissue specimen from a patient, the system comprising:
a retrieval bag having a flexible container with an opening;
a first electrode coupled to an interior of the flexible container, the first electrode configured to segment the tissue specimen into a plurality of tissue segments, the first electrode having a conductive wire with a coating having a first active electrode surface area, and an exposure area, the coating configured to provide a high impedance between the tissue specimen and the first electrode, wherein the first active electrode surface area is less than the exposure area; and
a return electrode; wherein
the exposure area comprises a region of the coating that has a plurality of micro voids, has an impedance that is less than the high impedance, has a reduced thickness, exposes the conductive wire, or any combination thereof; and wherein
at least a portion of the coating of the first electrode is configured to degrade during application of electrosurgical power to expand the first active electrode surface area.

26. A tissue removal system for extracting a tissue specimen from a patient, the system comprising:
a retrieval bag having a flexible container with an opening;
a first electrode coupled to an interior of the flexible container, the first electrode configured to segment the tissue specimen, the first electrode having a conductive wire with a first exposure area, a first load-bearing area, a coating having a first active electrode surface area and a high impedance area, wherein the first active electrode surface area is less than the first exposure area, and wherein an impedance between the first active electrode surface area and the tissue sample is less than an impedance between the high impedance area and the tissue sample;
an actuator coupled to the first electrode; and
a return electrode; wherein
the actuator is configured to selectively cause the first electrode to apply a first pressure on a tissue specimen placed within the retrieval bag and in contact with the first load-bearing area, the first pressure at least 275 kPa; and wherein
at least a portion of the coating of the first electrode is configured to degrade during application of electrosurgical power having a preselected power or voltage.

27. The tissue removal system of claim 26, wherein:
the portion of the coating of the first electrode comprises a plurality of micro voids, has a reduced thickness, exposes the conductive wire, or any combination thereof.

28. The tissue removal system of claim 26, further comprising:
a second electrode coupled to the interior of the flexible container, the second electrode having a conductive wire with a second exposure area, a second load-bearing area, a coating having a second active electrode surface area and a high impedance area, wherein the second active electrode surface area is less than the second exposure area; and wherein
the actuator is configured to selectively cause the second electrode to apply a second pressure on the tissue specimen in contact with the second load-bearing area, the second pressure at least 275 kPa.

29. A system for segmenting and removing a tissue specimen from a patient, the system comprising:
a retrieval bag having a flexible container with an opening; and
a first electrode coupled to an interior of the flexible container, the first electrode configured to segment the tissue specimen into a plurality of tissue segments, the first electrode having a conductive wire and a high impedance coating, the first electrode further having an active electrode surface; wherein
the high impedance coating is configured to degrade during an application of electrosurgical power to expand the active electrode surface.

30. The tissue removal system of claim 29, wherein:
the high impedance coating is configured to introduce an impedance between the high impedance coating and the patient, wherein the impedance is 100 Ohms or greater.

* * * * *